(12) United States Patent
Dupouy et al.

(10) Patent No.: US 10,509,945 B2
(45) Date of Patent: Dec. 17, 2019

(54) METHOD FOR QUANTITATIVE MEASUREMENT OF A BIOMARKER BY IN SITU IMMUNOFLUORESCENCE AND USES THEREOF

(71) Applicant: ECOLE POLYTECHNIQUE FEDERALE DE LAUSANNE (EPFL), Lausanne (CH)

(72) Inventors: Diego Gabriel Dupouy, Preverenges (CH); Ata Tuna Ciftlik, Morges (CH); Deborah Heintze, Lausanne (CH); Martin Gijs, Ecublens (CH)

(73) Assignee: ÉCOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 16/075,998

(22) PCT Filed: Feb. 8, 2017

(86) PCT No.: PCT/EP2017/052717
§ 371 (c)(1),
(2) Date: Aug. 7, 2018

(87) PCT Pub. No.: WO2017/137422
PCT Pub. Date: Aug. 17, 2017

(65) Prior Publication Data
US 2019/0347465 A1    Nov. 14, 2019

(30) Foreign Application Priority Data

Feb. 8, 2016 (EP) .................................... 16154745

(51) Int. Cl.
*G06K 9/00* (2006.01)
*G01N 33/574* (2006.01)
*G06T 7/00* (2017.01)

(52) U.S. Cl.
CPC ... *G06K 9/00127* (2013.01); *G01N 33/57484* (2013.01); *G06T 7/0014* (2013.01)

(58) Field of Classification Search
USPC ................................................ 382/128, 133
See application file for complete search history.

(56) References Cited

U.S. PATENT DOCUMENTS

| | | | | |
|---|---|---|---|---|
| 6,986,993 B1 * | 1/2006 | Ghosh | ................ | G01N 21/6428 435/288.7 |
| 7,219,016 B2 * | 5/2007 | Rimm | ................ | G01N 21/6458 702/19 |

(Continued)

FOREIGN PATENT DOCUMENTS

| | | |
|---|---|---|
| WO | WO 02/086498 | 10/2002 |
| WO | WO 2013/148458 | 10/2013 |

OTHER PUBLICATIONS

Barak, V. et al. "Clinical utility of cytokeratins as tumor markers" *Clinical Biochemistry*, 2004, pp. 529-540, vol. 37.

(Continued)

*Primary Examiner* — Ishrat I Sherali
(74) *Attorney, Agent, or Firm* — Saliwanchik, Lloyd & Eisenschenk

(57) ABSTRACT

The invention relates to a method for quantitative measurement of a biomarker by in situ immunofluorescence and uses thereof. In particular, the invention relates to a method which is a useful tool for use in the field of diagnosis, prevention and/or treatment of disease or disorders, in particular in the field of cancer management and therapy.

19 Claims, 18 Drawing Sheets

(56) References Cited

U.S. PATENT DOCUMENTS

| | | | | |
|---|---|---|---|---|
| 8,168,602 | B2* | 5/2012 | DePinho | C12Q 1/6886 514/44 A |
| 9,778,263 | B2* | 10/2017 | Bhaumik | G01N 33/57492 |
| 10,055,840 | B2* | 8/2018 | Chukka | G06K 9/0014 |
| 2013/0338016 | A1* | 12/2013 | McDonough | G01N 33/582 506/8 |
| 2017/0262984 | A1* | 9/2017 | Barnes | G06K 9/00147 |

OTHER PUBLICATIONS

Becker, K-F. et al. "Quantitative protein analysis from formalin-fixed tissues: implications for translational clinical research and nanoscale molecular diagnosis" *Journal of Pathology*, 2007, pp. 370-378, vol. 211.

Camp, R. L. et al. "Automated subcellular localization and quantification of protein expression in tissue microarrays" *Nature Medicine*, Nov. 2002, pp. 1323-1328, vol. 8, No. 11.

Carvajal-Hausdorf, D. E. et al. "Quantitative measurement of cancer tissue biomarkers in the lab and in the clinic" *Laboratory Investigation*, 2015, pp. 385-396, vol. 95.

Ciftlik, A. T. et al. "Microfluidic processor allows rapid HER2 immunohistochemistry of breast carcinomas and significantly reduces ambiguous (2+) read-outs" *PNAS*, Apr. 2, 2013, pp. 5363-5368, vol. 110, No. 14.

Dupouy, D. G. et al. "Continuous quantification of HER2 expression by microfluidic precision immunofluorescence estimates HER2 gene amplification in breast cancer" *Scientific Reports*, Feb. 9, 2016, pp. 1-10, vol. 6, No. 20277.

Dupouy, D. G. et al. "Rapid IHC Microfluidic Protocol Allows the Detection of Cancer Cells at the Margins of Surgical Cuts" µTAS 2015 poster, Gyeongju, Korea, p. 1.

Gustavson, M. D. et al. "Standardization of HER2 Immunohistochemistry in Breast Cancer by Automated Quantitative Analysis" *Archives of Pathology & Laboratory Medicine*, Sep. 2009, pp. 1413-1419, vol. 133.

Ha, T. et al. "HER2 Expression and Gene copy analysis by Immunofluorescence and Fluorescence in situ Hybridization, on a single formalin-fixed paraffin-embedded tissue section" *Cancer Research*, Dec. 15, 2012, p. 304s, vol. 72, 24 Suppl., P3-05-05.

McCabe, A. et al. "Automated Quantitative Analysis (AQUA) of In Situ Protein Expression, Antibody Concentration, and Prognosis" *Journal of the National Cancer Institute*, Dec. 21, 2005, pp. 1808-1815, vol. 97, No. 24.

Rimm, D. L. "What brown cannot do for you" *Nature Biotechnology*, Aug. 2006, pp. 914-916, vol. 24, No. 8.

Written Opinion in International Application No. PCT/EP2017/052717, dated Apr. 4, 2017, pp. 1-5.

* cited by examiner

Multiplying the «binary» value of the pixels of the first screening (e.g. CK) probe signal with the value of the second screening (e.g.DAPI) probe signal | S7

*Tile – first screening probe (e.g. CK) mask 6*

| 1 | 1 | 1 | 1 | 1 |
|---|---|---|---|---|
| 0 | 1 | 1 | 1 | 1 |
| 1 | 1 | 1 | 0 | 0 |
| 1 | 1 | 1 | 1 | 1 |
| 1 | 1 | 1 | 1 | 1 |

*Tile – second screening probe (e.g. DAPI) mask 7*

| 1 | 1 | 1 | 1 | 1 |
|---|---|---|---|---|
| 0 | 1 | 1 | 1 | 1 |
| 1 | 1 | 1 | 0 | 1 |
| 1 | 1 | 1 | 1 | 1 |
| 1 | 0 | 1 | 1 | 1 |

5

4                                                  4

| 1 | 1 | 1 | 1 | 1 |
|---|---|---|---|---|
| 0 | 1 | 1 | 1 | 1 |
| 1 | 1 | 1 | 0 | 0 |
| 1 | 1 | 1 | 1 | 1 |
| 1 | 0 | 1 | 1 | 1 |

*Tile of the Target evaluation mask (e.g. Epithelial cell mask)*

Tile of a Target evaluation mask
*(e.g. Epithelial cell mask)*

| 1 | 1 | 1 | 1 | 1 |
|---|---|---|---|---|
| 0 | 1 | 1 | 1 | 1 |
| 1 | 1 | 1 | 0 | 0 |
| 1 | 1 | 1 | 1 | 1 |
| 1 | 0 | 1 | 1 | 1 |

8

Tile with raw signal values for each pixel

| C11 | C12 | ..... | ..... | C15 |
|-----|-----|-------|-------|-----|
| C21 | ..... | ..... | ..... | ..... |
| ..... | ..... | ..... | ..... | ..... |
| ..... | ..... | ..... | ..... | ..... |
| C51 | ..... | ..... | ..... | C55 |

4

Product of target evaluation mask with raw values of first screening (e.g. CK) probe signal for each pixel  S8a

| C11 | C12 | ..... | .... | C15 |
|-----|-----|-------|------|-----|
| 0 | ..... | ..... | ..... | ..... |
| C31 | ... | ..... | 0 | 0 |
| ..... | ..... | ..... | ..... | ..... |
| C51 | 0 | .... | .... | C55 |

*Screening (e.g.CK) probe signal data for each pixel*

Tile of a Target evaluation mask (e.g. Epithelial cell mask)

| 1 | 1 | 1 | 1 | 1 |
|---|---|---|---|---|
| 0 | 1 | 1 | 1 | 1 |
| 1 | 1 | 1 | 0 | 0 |
| 1 | 1 | 1 | 1 | 1 |
| 1 | 0 | 1 | 1 | 1 |

8

Tile with raw signal values for each pixel

| T11 | T12 | ..... | ..... | T15 |
|---|---|---|---|---|
| T21 | ..... | ..... | ..... | ..... |
| ..... | ..... | ..... | ..... | ..... |
| ..... | ..... | ..... | ..... | ..... |
| T51 | ..... | ..... | ..... | T55 |

4

Product of target evaluation mask with raw values of target (e.g. HER2) probe signal for each pixel   S8b

| T11 | T12 | ..... | .... | T15 |
|---|---|---|---|---|
| 0 | ..... | ..... | ..... | ..... |
| T31 | ..... | ..... | 0 | 0 |
| ..... | ..... | ..... | ..... | ..... |
| T51 | 0 | .... | .... | T55 |

*Target (e.g. HER2) probe signal data for each pixel*

*Screening (e.g.CK) probe signal data for each pixel*

| C11 | C12 | ..... | .... | C15 |
|---|---|---|---|---|
| 0 | ..... | ..... | ..... | ..... |
| C31 | ... | ..... | 0 | 0 |
| ..... | ..... | ..... | ..... | ..... |
| C51 | 0 | .... | .... | C55 |

9

*Target (e.g.HER2) probe signal data for each pixel*

| T11 | T12 | ..... | .... | T15 |
|---|---|---|---|---|
| 0 | ..... | ..... | ..... | ..... |
| T31 | ..... | ..... | 0 | 0 |
| ..... | ..... | ..... | ..... | ..... |
| T51 | 0 | .... | .... | T55 |

10

Averaging of pixel values (not including the masked out values, e.g. of value zero) of each probe signal per tile

↓ S9a        ↓ S9b

*Tile with averge first screening probe signal*

*Tile with averge second screening probe signal*

Generation of sample output:
e.g. ratio of target signal / screening signal values; scatter plots; histograms; scoring e.g. based on a reference sample; etc

S12a

Generation of a scatter plot of target (e.g. HER2) probe signals vs screening (e.g. CK) probe signals

S12b

Calculation of ratios of target (e.g. HER2) probe signals over screening (e.g. CK) probe signals

S12c

Generation of Histograms representing the frequencies of said ratios normalized to the number of tiles Scoring of the sample  S12d

*Sample output 9*

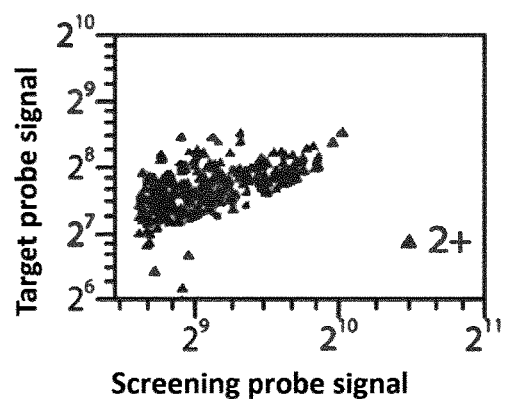

Screening probe signal

*Sample output 10*

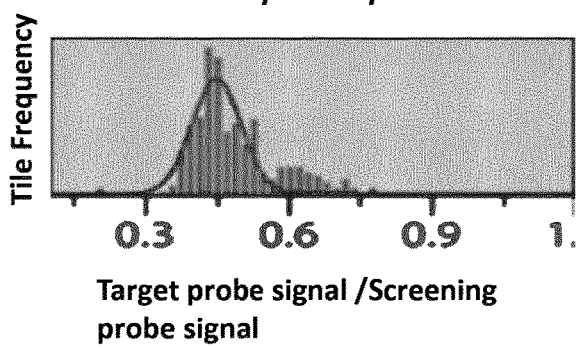

Target probe signal /Screening probe signal

| Case | Routine analysis | | MTP analysis | |
|---|---|---|---|---|
| | $N_{FISH}$ | Class. | HER2 / CK | MTP-score |
| 01 | 1.9 | Neg | | 0.04 |
| 11 | 4.4 | Equ | | 0.14 |
| 20 | 9.4 | Pos | | 0.56 |

Figure 5

METHOD FOR QUANTITATIVE MEASUREMENT OF A BIOMARKER BY IN SITU IMMUNOFLUORESCENCE AND USES THEREOF

CROSS-REFERENCE TO RELATED APPLICATION

This application is the U.S. national stage application of International Patent Application No. PCT/EP2017/052717, filed Feb. 8, 2017.

FIELD OF THE INVENTION

The present invention pertains generally to the fields of biomarkers and quantitative measurements thereof.

BACKGROUND OF THE INVENTION

Chromogens are molecules that allow detection of a target using enzyme-based precipitation reactions and their use in immunohistochemistry (IHC) allows visualization of the immune complex (and hence the antigen) in the context of tissue architecture. The most widely used chromogenic compound, 3,3'-diaminobenzidine (DAB), provides brown-colored staining, also commonly called "brown staining" (diaminobenzidine chromogenic staining or immunostaining). Optimal chromogenic staining relies on the deposition of a sufficient amount of substrate to block light. In the case of DAB, a "desirable' image" is regarded to be produced when deposition of the substrate leads to an absorbance of 1-2 units, meaning that 90 to 99% of the light signal is blocked. Although this creates a contrast that is easy to read, it hampers the use of multiple colocalized chromogens on routine assays (Carvajal-Hausdorf et al., 2015, *Laboratory investigation*, 95, 385-396).

Chromogenic IHC is omnipresent in cancer diagnosis but has been criticized for its technical limit in quantifying the level of protein expression on tissue sections, thus potentially masking clinically relevant data. Historically, the use of brown staining aimed at determining the presence or absence of a biomarker rather than intensity level of the staining. In fact, high levels of signal (staining) were even aimed at in order to ease the readings.

However, with the development of assays and treatments, assay read-outs no longer aim at a simple binary answer (expressed or not) but the quantification of the expression amount has also become a critical variable which is of high importance in the field of biomarkers, evolving from diagnostics to prediction of response to therapy. In this context, the limitations of immunodiagnostic assays have become more important (Rimm et al., 2006, *Nature Biotechnology*, 24, 914-916).

In particular, with the advancement of personalized cancer medicine, precise molecular profiling of tumors is gaining significant importance in routine diagnostic pathology and with the evolution towards personalized treatments tailored to the molecular features of malignant tumors, the last decade has witnessed an increasing use of molecular analysis approaches, including but not limited to in situ hybridization (ISH), mRNA expression profiling techniques and next generation sequencing (NGS). Immunohistochemistry (IHC), however, remains by far the most used method in the routine diagnostic evaluation of tumor tissues, with the advantages of wide availability, low cost, and preservation of the information-rich morphological context.

Continuous quantification of protein expression in tumor sections has long been the missing link between methods analyzing nucleic acids and conventional IHC. The majority of IHC tests currently used in clinical diagnosis cannot quantify the antigen (Ag) expression but rather perform a binary or semi-quantitative assessment as interpreted by the pathologist. An example of such semi-quantitative tests is the assessment of epidermal growth factor receptor 2 (HER2) protein expression level in breast cancer (known to promote the growth of cancer cells), for which the scoring can have four different levels: 0, 1+, 2+ or 3+(Wolf et al., 2013, *J. Clin. Oncol.*, 31, 3997-4013). Therefore, this non-continuous assessment results in a loss of information regarding the Ag expression level (Rimm, 2006, supra; Carvajal-Hausdorf et al., 2015, supra). Furthermore, it suffers from possible ambiguous, equivocal results and relative subjectivity in scoring between different pathologists.

To overcome the discrete nature of the semi-quantitative scoring methods, more continuous scoring algorithms such as the "H-score" have been proposed (Detre et al., 1995, *J. Clin. Pathol.*, 48, 876-878). These methods involve manually assessing the approximate sample areas with different levels of target biomarker expression (e.g. HER2) and multiplying the areas with appropriate "weights" according to the expression amount. However, this approach has other drawbacks such as the inability of the scorer to detect subtle differences in target expression especially at the low and high ends of the scale and the tendency to round scores, effectively converting the approach to another semi-quantitative one (Camp et al., 2002, *Nature Medicine*, 8, 1323-1328).

Techniques such as Western Blot and ELISA provide means for protein quantification but at the cost of the loss of morphological information and the integrity of the samples of interest since they require the lysing of the samples (Becker et al., 2007, *J. Pathol.*, 211, 370-378). While they potentially offer high reproducibility and accuracy, they are either regarded as complementary methods or utilized in assays for liquid media such as detection of circulating tumor elements in serum and therefore are less suitable for assessing protein expression levels in the morphological context of the tissue slide.

Genetic methods, particularly Fluorescent In-Situ Hybridization (FISH), are widely utilized as complementary techniques in cases of inconclusive results obtained with IHC or similar tests. Metrics such as the gene copy number provide quantitative information on the biomarker of interest. On the other hand, FISH is relatively expensive. Furthermore, the existence or amplification of a gene is a necessary but not a sufficient condition for the expression of a diagnostically relevant antigen biomarker. Comparison studies between IHC and FISH methods for HER2 have been widely performed in clinical research (Pauletti et al., 2000, *J. Clin. Oncol.*, 18, 3651-3664; Owens et al., 20014, *Clin. Breast Cancer*, 5, 63-69) and studies conclude that agreement between IHC and FISH is not complete, especially for IHC 2+ cases, creating issues with false positives and false negatives.

In this context, as clinical pathology moves from qualitative to quantitative, immunofluorescence (IF) is gaining relevance in the research settings and laboratory-developed tests, mainly due to its increased capacity to measure the signal intensity of one or more biomarkers as compared to traditional chromogenic techniques (Carvajal-Hausdorf et al., 2015, supra). Several image processing techniques that quantify the extent of IF signal have already been reported in the literature (McCabe et al., 2005, *JNCI J. Natl. Cancer*

*Inst.*, 97, 1808-1815; Rojo et al., 2010, *Folia Histochem. Cytobiol.* 47). However, there is little or no evidence suggesting that the IF signal per se can be used to precisely quantify Ag expression amount on tissue sections. Indeed, due to the kinetics of Ag-antibody (Ab) binding, a 2-step IF assay does not result in a signal that is linearly proportional to the Ag expression (Caelen et al., 2000, *Langmuir*, 16, 9125-9130; Squires et al., 2008, *Nat. Biotechnol.*, 26, 417-426), which potentially ends up in a misleading quantification and, hence, obscures the potential of IF in providing precise biomarker data.

Therefore, shifting from qualitative to quantitative, immuno fluorescence (IF) has recently gained attention, yet the question of how precisely IF can quantify antigen expression remains unanswered, regarding in particular its technical limitations and applicability to multiple markers. There is therefore a need to find precise methods that allow to routinely and precisely quantify biomarker expression in tissues while preserving the morphology since those methods would not only reduce the requirement for expensive complementary gene analysis but also increase the precision of diagnosis, prognosis and the success of targeted therapies, in clinical trials and routine patient care.

SUMMARY OF THE INVENTION

An object of this invention is to provide a method for quantifying by immunofluorescence the amount of a target marker present in a biological sample fixated on a support, which enables accurate quantification of the level of said marker in a continuous manner.

It is advantageous to provide a method of detection of a target marker by immunofluorescence where the immuno fluorescence signal is directly proportional to the said target marker's concentration.

It is advantageous to provide a method of detection of a target marker by immunofluorescence which enables the establishment of a linearly proportional relationship between the IF signal intensity and its antigen expression level.

It is advantageous to provide a method of detection of a target marker by immunofluorescence which enables continuous quantification of protein expression levels and can obtain a score correlated to the number of the corresponding protein expressing gene copy numbers in a reliable manner comparable as assessed by fluorescence in situ hybridization (FISH).

It is advantageous to provide a method of detection of a target marker by immunofluorescence which enables establishing a continuous scoring that linearly follows the gene copy number as assessed by fluorescence in situ hybridization (FISH) and which allows to provide additional information compared to FISH of particular interest for equivocal cases since the existence or amplification of a gene, while being necessary, is not sufficient for the expression of a diagnostically relevant antigen biomarker.

Objects of this invention have been achieved by providing a method according to claim 1.

Disclosed herein is a method for quantitative measurement of a target marker by in situ immunofluorescence comprising the steps of:
a) providing a sample immobilized on a sample support;
b) carrying out a staining step comprising incubating said sample with at least one target probe, at least one screening probe for imaging the sample region of interest (first screening probe) and optionally at least one further screening probe for the sample region of non-interest to be discarded in further analysis (second screening probe), wherein incubation times of the sample with each of said probes are sufficiently low to avoid saturation of the sample with the probes, while ensuring suitable staining of the sample so that a linear relationship between the target marker concentration and the resultant fluorescent signal intensity can be formed;
c) acquiring an image of the stained sample comprising raw signals emitted by each of the imaging probes;
d) generating a target evaluation mask comprising an active area for analysis of said target marker, comprising defining a threshold for signals of said at least one screening probe, and assigning binary values to screening probe signals, said binary values comprising a first value (for example 0) and a second value (for example 1), whereby screening probe signal values that are beyond said corresponding threshold are set to said first value, and screening probe signal values that are not beyond said corresponding threshold are set to said second value, said active area of the mask being defined by areas of the image comprising signals set to said second value;
e) applying the active area of the target evaluation mask on the raw signal values of the first screening probe to obtain a screening probe data set comprising values proportional to the raw signal values of the first screening probe for the active area;
f) processing signals of the target probe, including extracting target probe signal data limited to said active area to obtain a target probe data set comprising target probe signal values for the active area; and
g) generating a sample output including combining said target probe data set with said screening probe data set to provide information on quantitative levels of the target marker.

The method may advantageously further include:
processing said image before generating said target evaluation mask, comprising defining tiles representing surface area portions of the image; and
effecting steps (d) and (e) on each tile.

In an advantageous embodiment, a threshold is defined for each tile.

The threshold for a corresponding tile may be defined by means of a per se known autothresholding algorithm applied over said corresponding tile.

Raw signals emitted by each of the imaging probes may be raw signals of pixels of the image and wherein assigning screening probe signals to a first value or to a second value may be performed on each pixel.

In an embodiment, in step (e) the method may include calculating, for each tile, an average of the values proportional to the raw signal values of the first screening probe for the active area, to obtain an average first screening probe signal value per tile.

In an embodiment, the method may further comprise a second screening probe.

In an embodiment, the method may comprise defining a threshold for signals of said second screening probe, and assigning said binary values to the second screening probe signals, whereby second screening probe signal values that are beyond said corresponding threshold are set to the first value, and second screening probe signal values that are not beyond said corresponding threshold are set to the second value.

Generating a target evaluation mark may advantageously comprise multiplying the binary values corresponding to the first screening probe signals with binary values corresponding to the second screening probe signals.

In an embodiment, in step (e) the method may include filtering the screening probe data set, said filtering comprising defining a data set threshold, for instance by means of an autothresholding algorithm, and excluding data of the screening probe data set that are beyond said data set threshold, to obtain a filtered screening probe data set for a filtered active area.

The method may include filtering the target probe data set, said filtering comprising excluding data of the target probe data set such that a filtered active area covered by the filtered target probe data set matches the filtered active area covered by the filtered screening probe data set.

In an embodiment, in step (f), the method includes applying the active area of the target evaluation mask on the raw signal values of the target screening probe to obtain values proportional to the raw signal values of the target probe for the active area.

In an embodiment, the method may include calculating, for each tile, an average of the values proportional to the raw signal values of the target probe for the active area, to obtain an average target probe signal value per tile.

In an embodiment, generating sample output may comprise any one or more of:
- representing in a graph, for instance in the form of a scatter plot (9), values of the target probe signal versus values of the first screening probe signal for each tile;
- generating a histogram (10) representing the frequencies of occurrence of a ratio of target probe signal over the first screening probe signal for the sample;
- generating a score for the sample by comparing the output of said sample with outputs for a positive control sample (such as a cancer positive case) and a negative control sample (non-cancerous sample) obtained by a method according to any of the preceding claims;
- generating a score for the sample by comparing the output of said sample with target marker levels obtained by other methods.
- calculating ratios of target probe signals over the values of the first screening probe signals for each tile, and displaying the said ratios;
- generating a histogram (10) representing the frequencies of occurrence of a ratio of target probe signal over the first screening probe signal for the sample normalized to the number of tiles for a given sample.

In an advantageous embodiment,
- the first screening probe is an imaging probe for a marker of epithelial cells, for instance the first screening probe comprises an antibody specific for cytokeratin, such as anti-cytokeratin;
- the target probe is an imaging probe for a membrane-associated molecule of a cancer cell such as human epidermal growth factor receptor 2 (HER2), or anaplastic lymphoma kinase (ALK), for instance, the target probe comprises an imaging probe for an antibody specific for HER2 such as anti-cerb-2;
- optionally, the second screening probe is an imaging probe for a marker for the cells' nucleus, for instance the second screening probe is a dye specific for the cells' nucleus such as DAPI (4,6-diamidino-2-phenylindole).

In an embodiment, in step c), the method comprises acquiring images of the stained sample comprising imaging a signal emitted by each of the said imaging probes, i.e. the first screening probe signal, optionally the second screening probe signal and the target probe signal.

In an embodiment, the threshold is a fixed value or obtained by an autothresholding step.

In an embodiment, the method comprises an image processing step before generating the target evaluation mask, comprising creating images of sample surface area units ("tiles") and creating raw signal values files of each raw signal values for each imaging probe signal for each pixel of each tile.

In an embodiment, the incubation times of the sample with each of said probes are advantageously not higher than 16 minutes in order to avoid saturation of the sample.

In an embodiment, the incubation times of the sample with each of said probes may be less than 8 minutes, for example between 1 and 5 minutes.

In an embodiment, the incubation times of the sample with each of said probes are not higher than about 3-5 min (typically incubation times of about 1 to 3 min) to obtain a stained sample.

In a particular embodiment, the staining step comprises the incubation in sequence with a plurality of reagents, including:
- at least one first screening probe;
- at least one target probe; and
- at least one second screening probe;

wherein said incubation in sequence with a plurality of reagents includes:
- an optional elution step where an elution buffer is eluted against the sample for removing undesirable material such as probes used in previous steps potentially remaining on the sample before starting the incubation with the first probe;
- a washing step wherein a washing buffer is flowed on the sample preceding and following the incubation of the sample with of each of the probes, wherein flow times during each washing step between the sample and the washing buffer is about 10-15 s.

In another particular embodiment, the staining step comprises the incubation in sequence of the sample with a plurality of imaging probes according to the invention wherein the incubation with probes is in the following sequence: first screening probe for imaging the sample region of interest, target probe for imaging the target marker and second screening probe for imaging the sample region to be discarded for analysis.

In an embodiment, the elution step or washing step are conducted at a flow rate between about 0.2 nl/s and about 25 μl/s.

In an embodiment, the incubation of the sample with each of said probes is conducted at a temperature from about 25 to about 60° C.

In another embodiment, the imaging probe is a labelled probe suitable for interacting with specific molecular entities on the sample (e.g. target maker such as expressed protein, screening marker such as a marker for a certain cell type, or a cell compartment, a screening marker such as a cell compartment marker such a marker for the nucleus, cytoplasm, membrane etc.). For example, an imaging probe can be a labeled RNA or DNA sequence useful for hybridizing in-situ with RNA or DNA sequences from the sample (complementary sequences). In another example, the imaging probe is a labeled primary antibody (e.g. fluorescent), which binds directly the target antigen or indirectly such as those used in Tyramid Signal Amplification (TSA).

In another embodiment, the imaging probe results from the incubation with a sequence of labelling probes such as specific antibodies and chromogenic or fluorescent detection molecules, targeting the molecular entities to be analyzed within the sample. In one embodiment, the imaging probe results from a labeled secondary (e.g. fluorescent) antibody that is incubated after a primary antibody.

According to a particular embodiment, the first screening probe is an imaging probe for a marker of epithelial cells.

According to a further particular embodiment, the first screening probe comprises an antibody specific for cytokeratin, such as anti-cytokeratin.

According to another particular embodiment, the target probe is an imaging probe for a membrane-associated molecule of a cancer cell such as human epidermal growth factor receptor 2 (HER2), anaplastic lymphoma kinase (ALK).

According to further particular embodiment, the target probe is an imaging probe for human epidermal growth factor receptor 2 (HER2).

According to a further particular embodiment, the target probe is an imaging probe for an antibody specific for HER2 such as anti-cerb-2.

According to another particular embodiment, the second screening probe is an imaging probe for a marker for the cells' nucleus.

According to a further particular embodiment, the second screening probe is a dye specific for the cells' nucleus such as DAPI (4,6-diamidino-2-phenylindole).

According to a particular embodiment, the sample output generation step, comprises a step of comparing the sample output for the analyzed sample with the same output obtained by the method of the invention on a positive control sample (such as a cancer positive case) and a negative sample (e.g. non-cancerous sample).

According to a particular embodiment, the sample output generation step comprises representing the values of the ratios of target probe signal over the values of the first screening probe signal. In a more particular embodiment, the sample output generation step comprises the representation of the frequencies of occurrence of a particular ratio (value of target probe signal over the value of the first screening probe signal) over the sample (i.e. number of tiles presenting such ratio) normalized to the number of tiles for a given sample (e.g. histogram).

According to a further particular aspect, a Gaussian fit is applied to the obtained histograms and the mean value of the ratios (value of target probe signal over the value of the first screening probe signal) is derived from this Gaussian fit and then normalized by the mean value obtained on a positive control sample (e.g. cancerous sample) for defining the mean score of the analyzed sample (M-score).

According to a further particular aspect, the standard deviation ($\sigma$) of the said Gaussian fit is normalized by the standard deviation of a positive control sample (e.g. cancerous sample) for defining the standard deviation score ($\Sigma$-score) of the analyzed sample.

According to a further particular aspect, a sample score (MTP-score) is assigned to the analyzed sample by multiplying the so-obtained M- and $\Sigma$-scores. In a more particular embodiment, the MTP-score correlates with the amount of overexpression of the target in the sample.

The above mentioned features may be combined in any appropriate manner.

An advantageous characteristic of the invention is to provide a method which can quickly replace routine chromogenic stain-based diagnostic IHC, since it would use the same primary antibodies, established sample preparation techniques and, hence, can be easily implemented in current laboratory practice without too drastic changes.

A noticeable advantage of the method of the invention is for providing automated and precise continuous quantitative in situ target marker (e.g. biomarker) information using low-cost immunofluorescence assays, as increasingly required for personalized cancer therapy.

According to a further aspect, the method can be applied to all markers, notably in the field of cancer diagnosis.

Other features and advantages of the invention will be apparent from the claims, detailed description, and figures.

a: Steps S1 to S6: staining the sample with at least one target probe, at least one screening probe for imaging the sample region of interest (first screening probe) and optionally at least one further screening probe for the sample region of non-interest to be discarded for further analysis (second screening probe); acquiring images of the stained sample, forming image tiles based on the obtained images, processing the images where a tile-specific threshold filter is applied to each pixel comprising setting to a first value (e.g. 0) pixels having a screening probe signal beyond the thresholds that need to be discarded and to a second value (e.g. 1) to the retained pixels;

b: Step S7: creating a target evaluation mask on the tile;

c & d: Steps S8a and 8b: creating a data set for screening probe signals $C_{11}$ to Cjj (1c) and target probe signal $T_{11}$ to Tjj (1d) for each pixel (1 to j) over each tile;

e: Steps S9a and 9b: averaging the data sets of screening probe signals over the tile to an average value $C_a$, and averaging the data sets of target probe signals over the tile to an average value $T_{av}$ to create a screening probe signal data matrix with all the average values $C_{av}$ ($C_{av11}$ to $C_{avnn}$) and a target probe signal data matrix with all the average values $T_{av}$ ($T_{av11}$ to $T_{avnn}$) for all the tiles (1 to N);

f: Step S10: applying a threshold filter ("autothreshold") to the screening probe signal data matrix comprising setting to a first value (e.g. 0) tiles having a screening probe signal beyond the thresholds and need to be discarded and to a second value (e.g. 1) the retained tiles (S10a) to form a filtered first screening probe signal data matrix; Mirroring the resulting filtered first screening probe signal data matrix on the target probe signal data matrix obtained under step S9b to form a filtered target probe signal data matrix (S10b) to retain only the data for target probe signal for the tiles retained on the basis of their first screening probe signal;

g: Step S11: data binning on both filtered first screening probe signal data and target signal data matrices and generation of sample output data;

h: Steps S12a-d: generation of sample output including comparing scoring of the analyzed sample;

i: Overview of the image analysis steps S4 to S12 iterated over the entire tile set (N) of the sample image of the method of the invention using target (HER2) probe signal, first screening (CK) probe signal and second screening (DAPI) probe signal.

Figure 2:
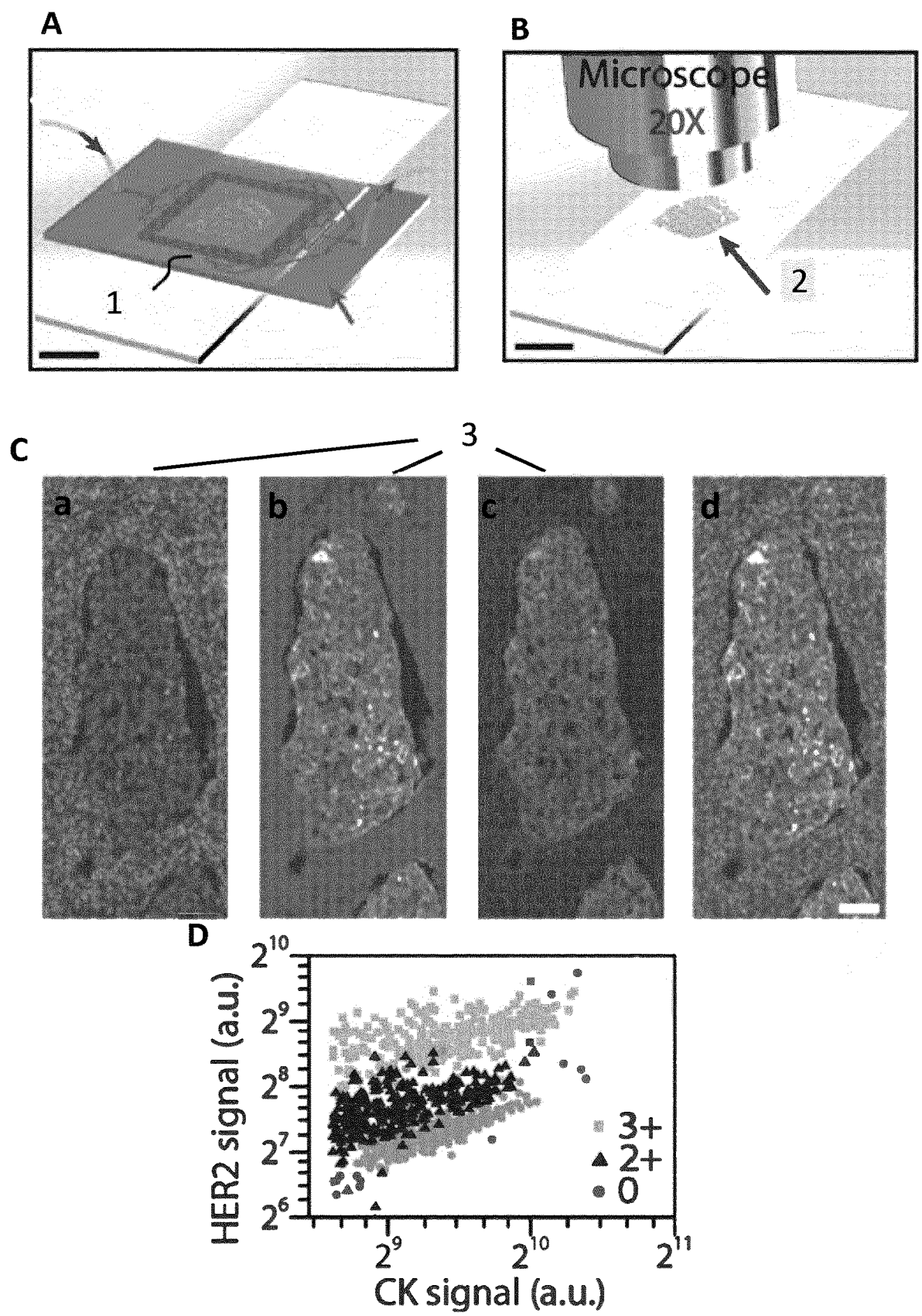

FIG. 2 is an illustration of the method of the invention using immunofluorescence imaging of a breast tumor surgically resected in the form of thin histological tissue slides for analysis as described in Example 1 and analyzed as described in Example 2.

A: Sample slide is clamped (biological sample immobilized on a sample support (1)) on a microfluidic device and applied short incubation times with imaging probes for IF staining (S2);

B: The stained sample (2) is imaged using a fluorescent microscope (S3);

C: Mosaic images (3) of the stained sample acquired in 3 fluorescent channels, corresponding to the signals of the second screening probe: DAPI (a), the first screening probe: CK (b), and the target probe: HER2 (c) and the merge by superimposition of the images (a) to (c) leading to image (d), respectively which are automatically and tile-by-tile analyzed (S5-S12).

D: 2D scatter plot (S12a) showing the correlation between the averaged HER2 and CK signal per tile, for three samples with different IHC score obtained from routine analysis: 3+(squares), 2+(triangles) and 0 (dots). Scale bars: 10 mm for A & B, 100 μm for C.

Figure 3:
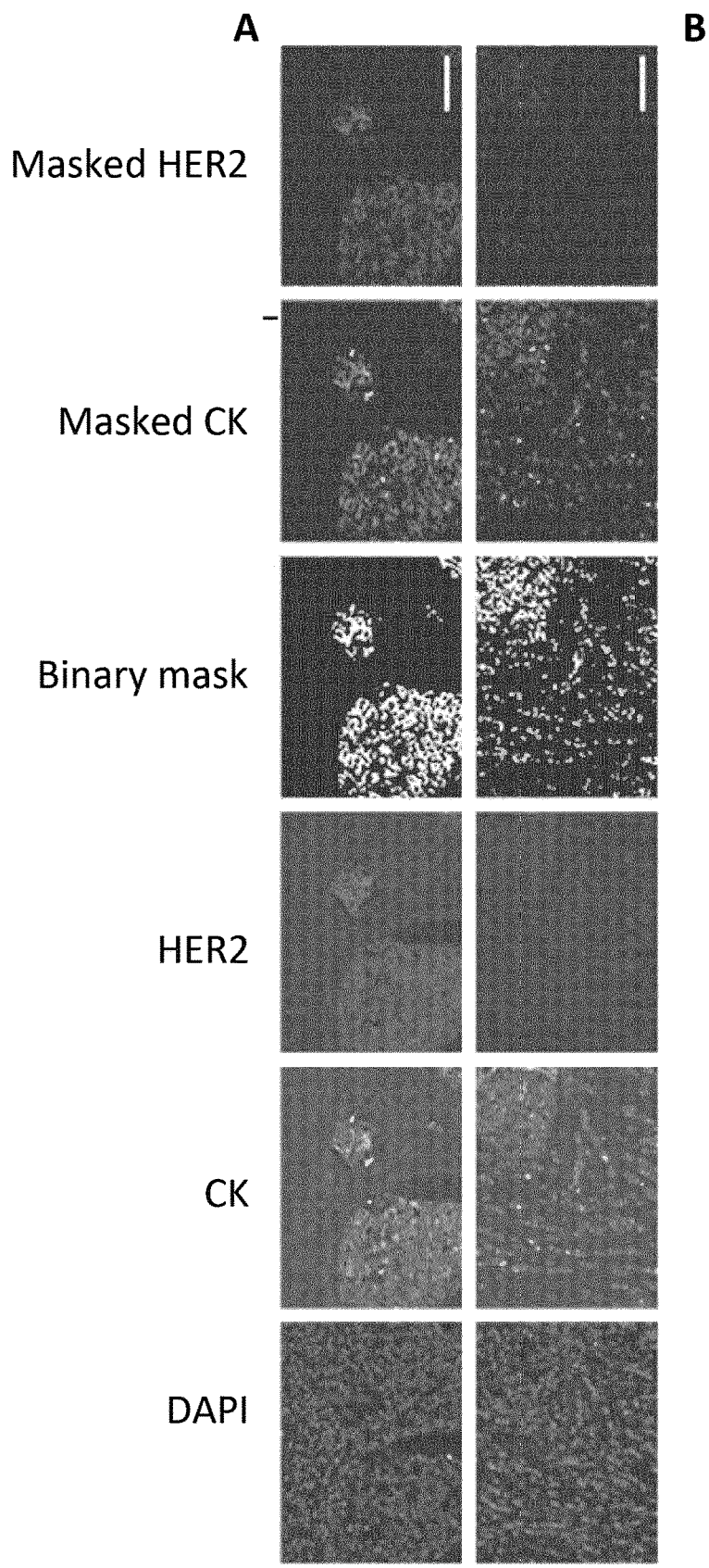

FIG. 3 is an illustration of a step of target evaluation (binary) mask applied on image tile processing in a method of the invention. The image processing is applied to a case where HER2 is overexpressed (A) and not expressed (B). The image processing uses DAPI channel to mask the locations of the nuclei ("DAPI mask"), while the CK channel indicates the location of epithelial cells, i.e. exactly the areas where the HER2 and CK signals should be interrogated ("CK mask"). This allows constructing a binary mask where the pixels of the tile appear then as black (discarded) or white (retained) and by applying this mask to the raw values, one obtains the masked tile from which can be extracted an average signal for the each of the CK and HER2 signals, obtained from the areas of interest only. Scale bar: 100 μm.

Figure 4:
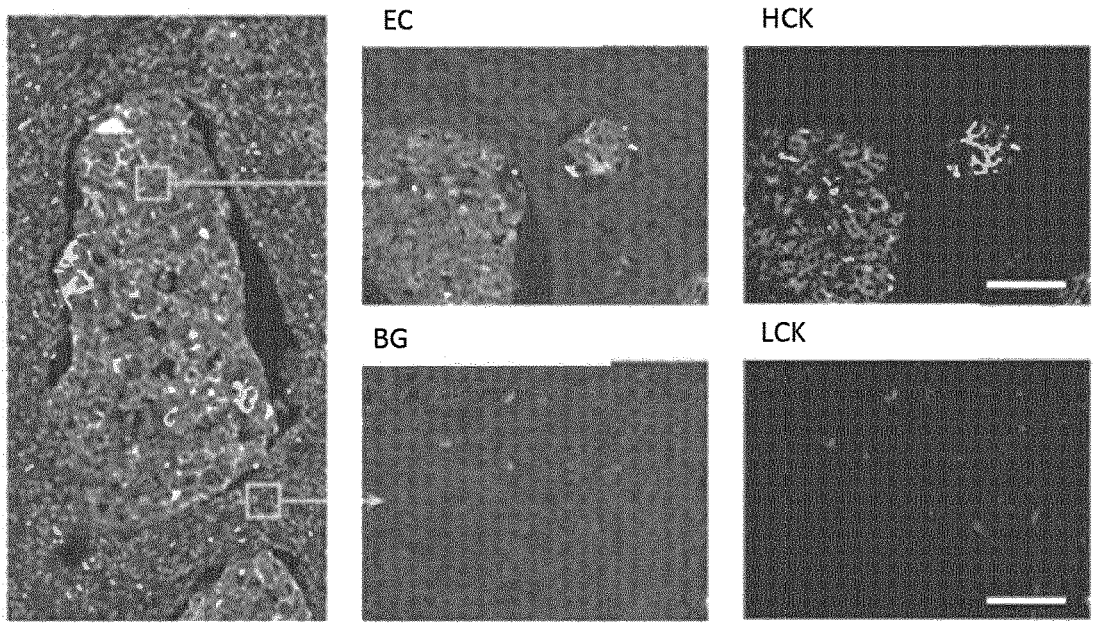
Figure 4:
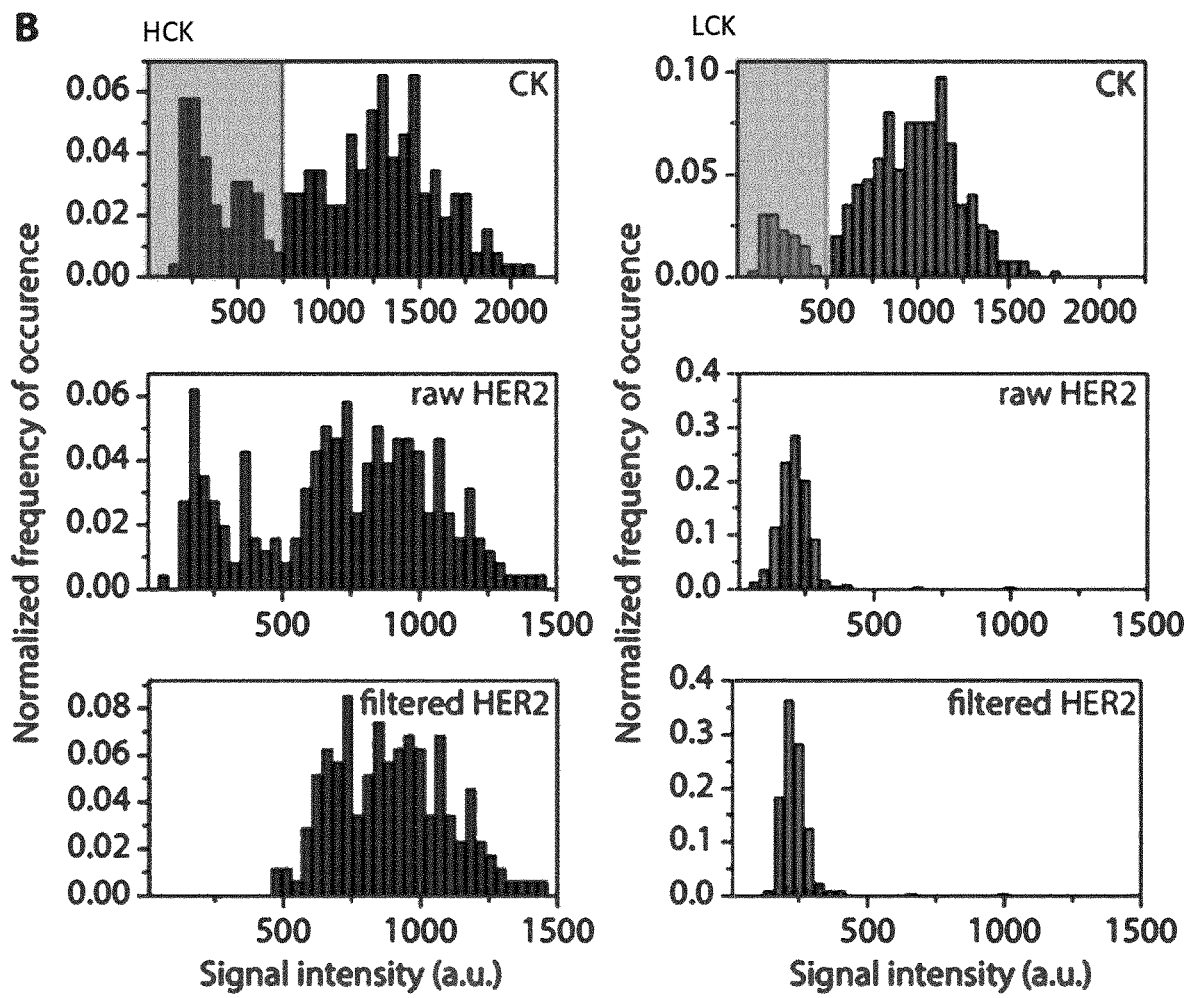

FIG. 4 is an illustration of an autothresholding step (S10a) based on CK signal intensity for removing tiles showing low CK signal from the data set for further analysis. A: Example of tissue areas with (top) and without (bottom) epithelial cells and visualized in the raw CK channel (two middle images: epithelial cells (EC) area, background area (BG)) and after running the image processing algorithm (two right images: high CK signal (HCK) and low CK signal (LCK)). B: Raw histograms of the intensity distribution of the CK (first row) and HER2 (second row) signals for a HER2 IHC $3^+$ case (left column) and a HER2 $IHC^0$ case (right column). Third row: HER2 histograms plotted after application of this CK filter where the tiles with a low CK signal intensity have been removed from the histogram for further analysis.

FIG. 5 represents scatter plot signatures obtained by the immunofluorescence method according to the invention (HER2 and CK signals: triangles) compared with the immunofluorescence signal obtained from the IHC3+ (squares) and IHC0 (dots) control samples of the batch, together with the corresponding HER2 gene copy number for 3 of the 25 invasive breast carcinoma cases as described in Example 2. The listed values for the cell-averaged HER2 gene copy number ($N_{FISH}$) were obtained from FISH routine analysis. HER2 status classification (Class) by the pathologist based on $N_{FISH}$ as follows: $N_{FISH}$<4: Negative; $4 \leq N_{FISH}$<6: Equivocal; $N_{FISH} \geq 6$: Positive.

Figure 6:
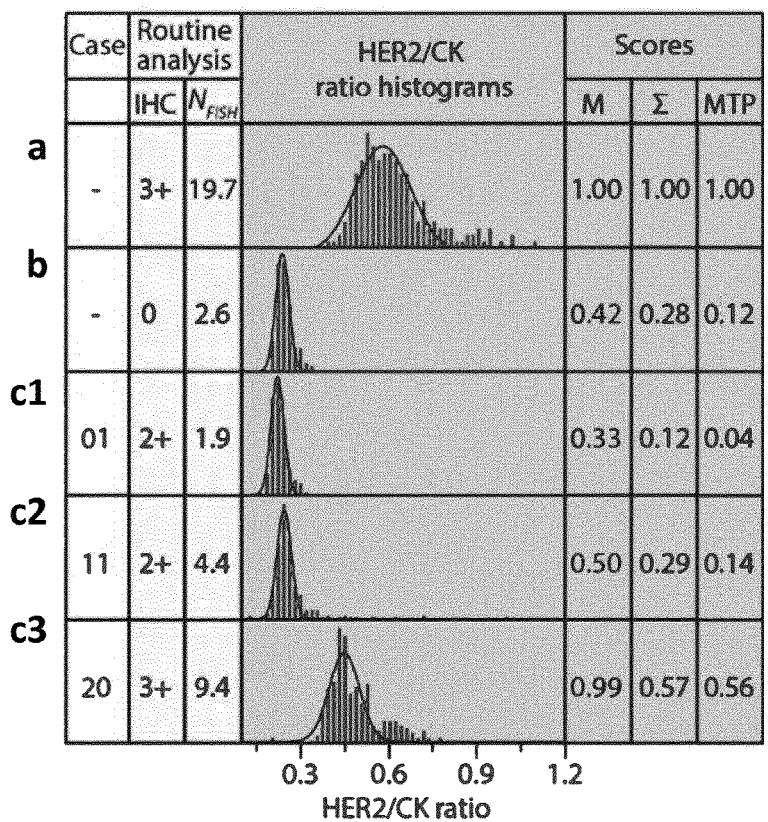

FIG. 6 shows a comparison of histograms of borderline and control cases as described in Example 2 with the following IHC scores: One 3+ case (a), one 0 case (b), and three borderline cases (c1-c3). M-score: Mean value of the Gaussian fit of the histogram determining the mean HER2/CK value normalized by the mean of the 3+ control sample in the batch; Σ-score: Standard deviation (σ) of the Gaussian fit, normalized by σ of the 3+ control sample; MTP-score: product of the M- and Σ-scores.

Figure 7:
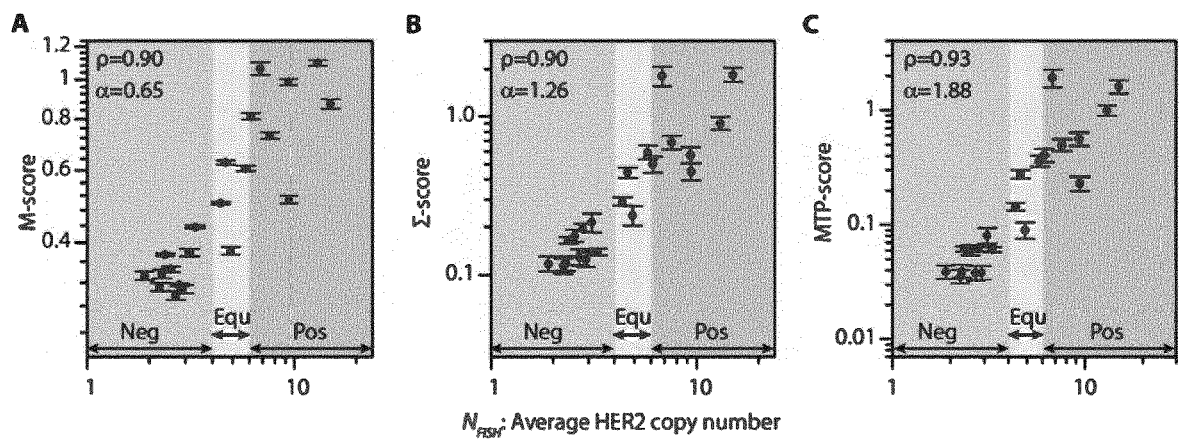

FIG. 7 shows that the MTP-Score can estimate N $F_{FISH}$ with a high confidence. A: M-score, B: Σ-score; C: MTP-score vs N $F_{FISH}$. HER2 status classification according to routine FISH analysis is indicated by the greyed zones, representing from left to right negative (Neg), equivocal (Equ) and positive (Pos) cases, respectively. ρ and α represent Pearson's coefficients and slopes of the power law fits, respectively. Error bars are obtained from Gaussian fits to the histogram data.

Figure 8:
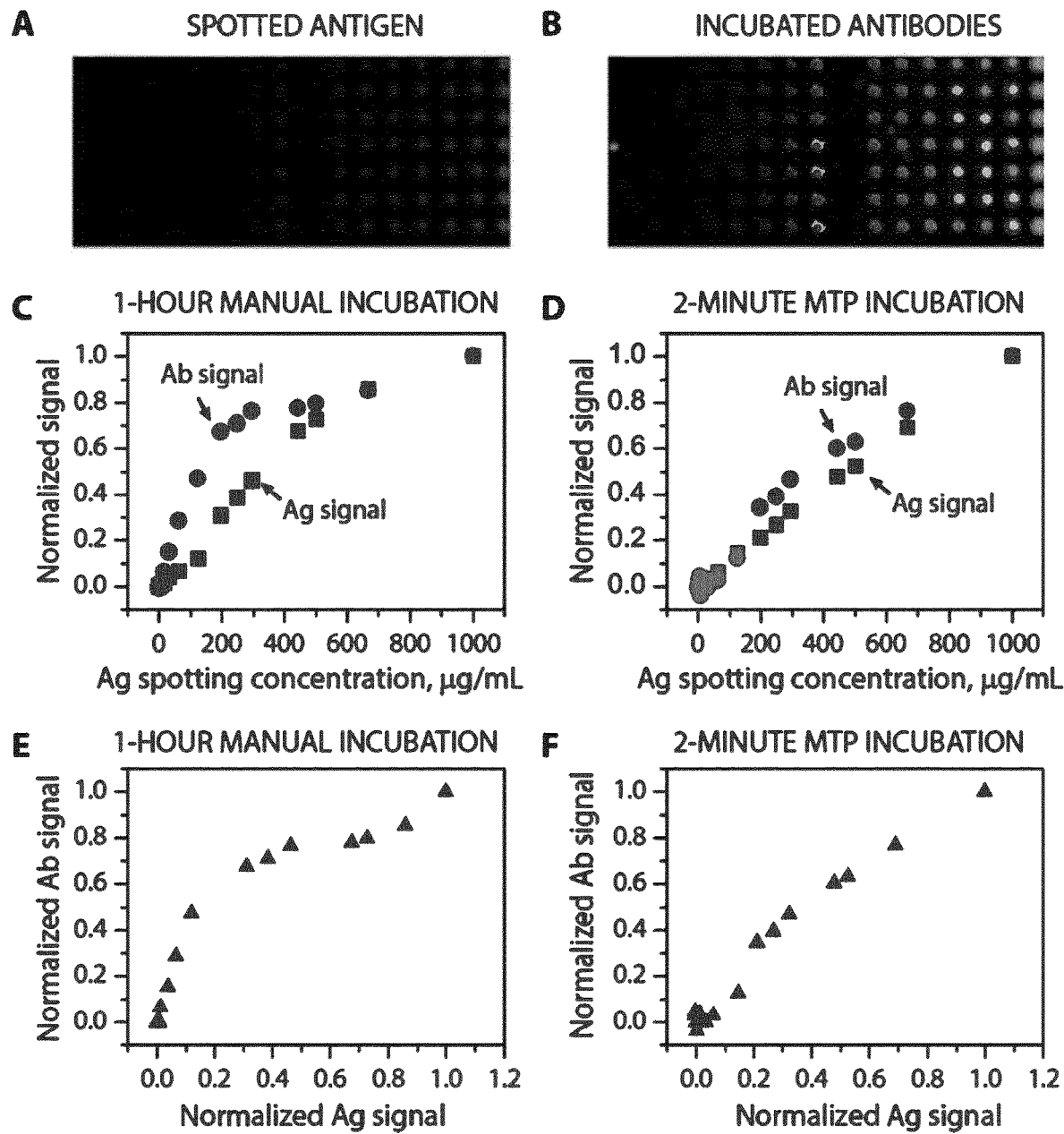

FIG. 8 shows the effect of the Ab incubation time on the proportionality of Ag and Ab signals. A: Fluorescent image of AF647 mouse antibodies used as Ag and spotted on an epoxy-functionalized glass slide with a concentration ranging from 0 to 1000 μg/mL; B: Fluorescent image of AF488 anti-mouse antibodies, used as Ab delivered and incubated using the MTP; C & D: normalized fluorescent signals of the spotted Ag and its recognizing Ab for an 1 h and 2 min incubation time, respectively, versus the Ag spotting concentrations; E & F: normalized fluorescent signals of the recognizing Ab versus the signals of the spotted Ag for an incubation time of 1 h and 2 min, respectively.

Figure 9:
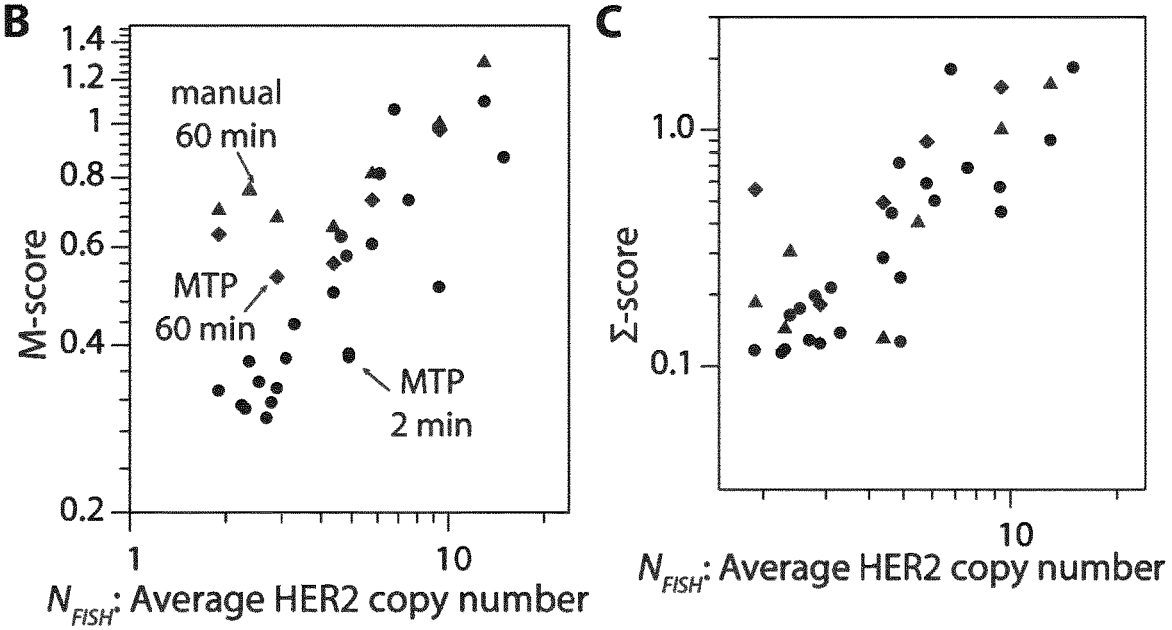

FIG. 9 shows the comparison of the use of short vs long Ab incubation times for accurate IF analysis. A: Histograms of the HER2/CK ratio obtained with (i) the method of the invention (MTP) using short incubation times, or (ii) an off-chip protocol using an incubation time of 1 hour; B: M-score plot; C: E-score plot. The triangle-shaped data points correspond to experiments done with the 1 hour incubation time, while the circular data points were obtained using a 2 min incubation time protocol in a microfluidic device as described herein. The diamond shaped data points represent additional control stains done with the MTP using a long incubation time of 1 hour.

Figure 10:
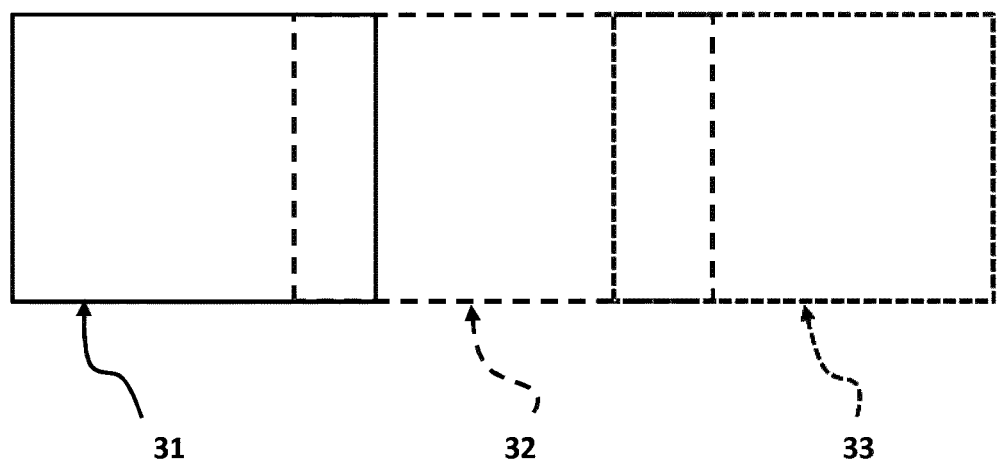
Figure 10:
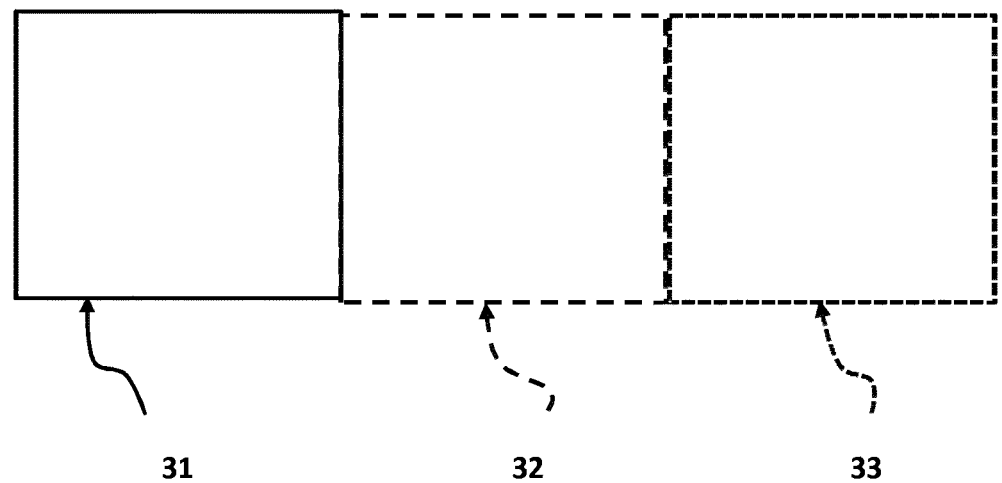
Figure 10:
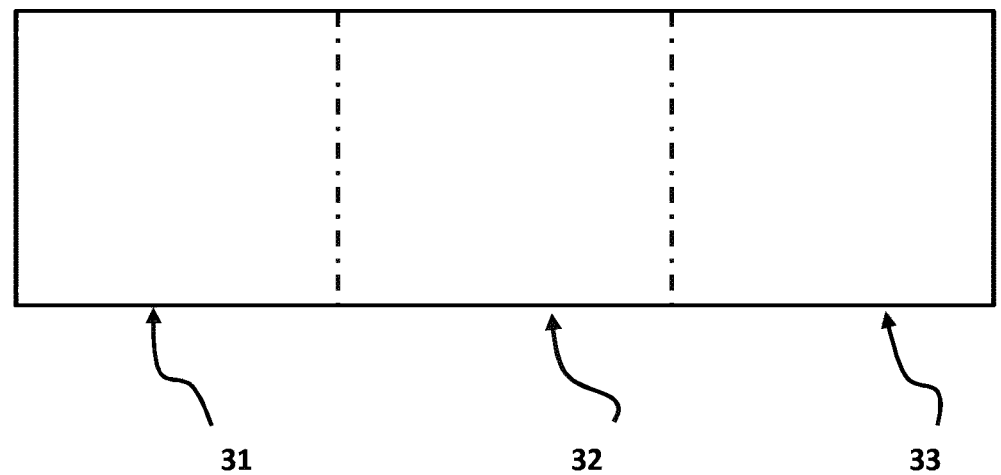
Figure 10:
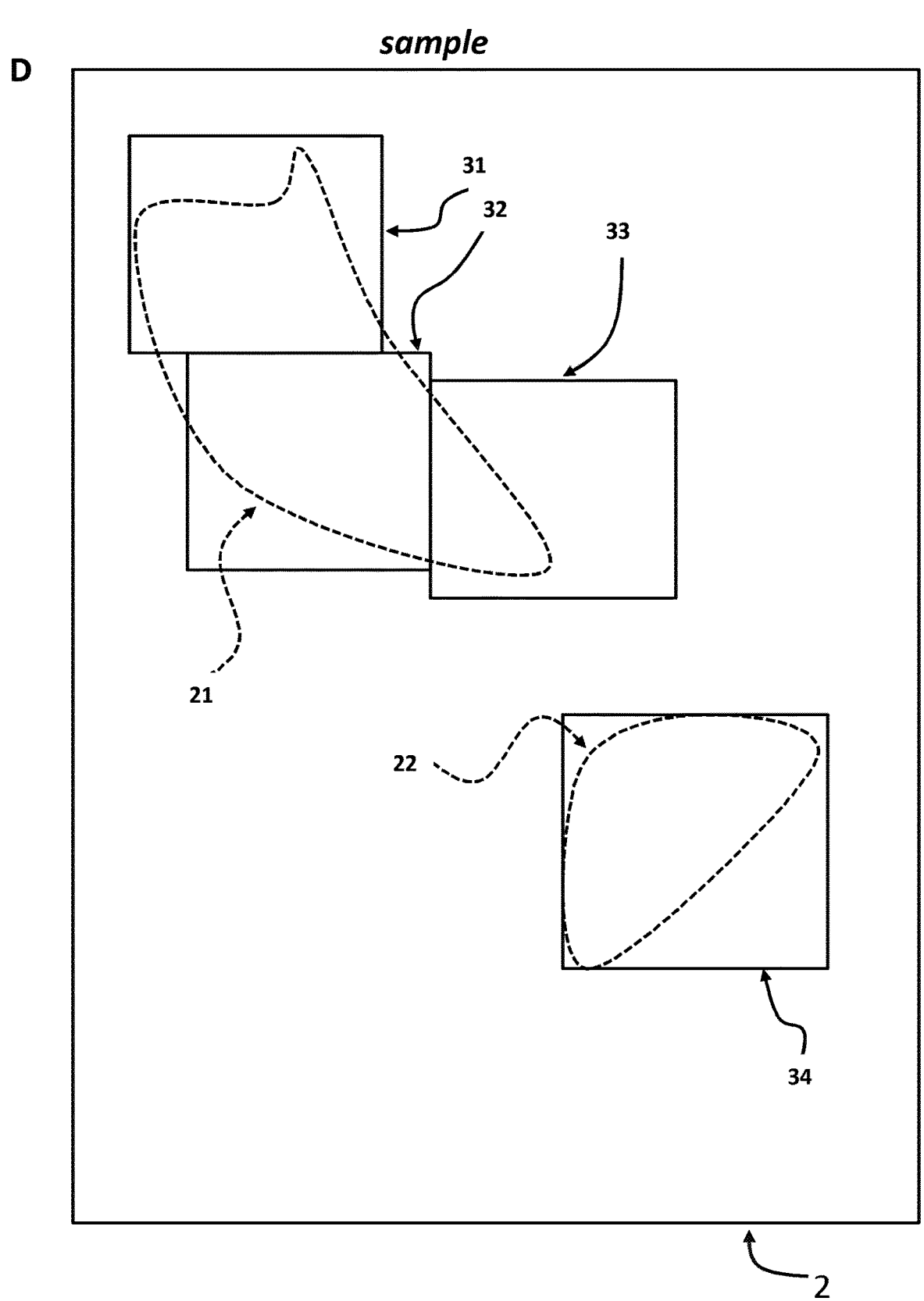

FIG. 10 illustrates schematically examples of possible tile generation processes, wherein the signal information of tiles 31, 32, 33, 34 originates from successive images taken either from overlapping (A) or non-overlapping areas (B and D) on a stained sample, wherein those areas can be selected areas of interest 21, 22 of the sample (D) and recombined in a single image which can subsequently be tiled (C).

DETAILED DESCRIPTION OF THE INVENTION

The term "sample" according to the invention refers to a biological sample immobilized on a sample support which includes biological samples derived from a tissue, fluid or secretion of the biological source, such as biopsy tissue samples, histology tissue samples, cell smears, needle biopsy samples or tissue microarrays.

The term "tile" according to the invention refers to a portion of an image from a sample surface area. The portion of image represented by a tile might correspond to an acquired image of a surface portion of interest from the sample, or the portion of image represented by a tile may be obtained by subdividing an acquired image of the sample surface area into portions.

The term "tiling" according to the invention refers to generating portions of an image of a sample over a sample surface area or to generate portions of an image of the sample. Examples of tiling process are illustrated on FIG. 10.

The term "data binning" according to the invention refers to a known process in data processing which comprises allocating a single value to each of all the values comprised within a certain range of values.

The term "screening probe" refers to an imaging probe which allows imaging a sample region of specific interest or a sample region to be discarded for further analysis.

The term "target probe" refers to an imaging probe which allows imaging a target marker of specific interest within the sample. For example, a target marker is a protein, DNA, RNA marker which is present in a cell or a tissue and would be indicative of a disorder. For example, a target marker according to the invention is a protein expressed by a cancer cell.

The term "marker" is a distinctive biological or biologically derived indicator of a process, event, or condition or of a specific cell or tissue compartment or area.

The term "target marker" is a marker of interest for analysis which is indicative of a process, event, or a certain condition (as aging, disease, or exposure to a toxic substance, treatment or disease progression status) in a cell or biological sample or tissue which is useful for obtaining information useful for the diagnosis, prevention and/or treatment of disease or disorders.

According to a particular embodiment, target markers are markers of cancer cells.

According to a further embodiment, target markers are cancer cell membrane-associated molecules.

According to a further embodiment, target markers are markers which are predominantly present in cancer cells of epithelial origin (carcinomas).

According to a further embodiment, target markers are markers predominantly present in cancer cells from epithelial origin selected from PanCK (AE1-AE3), ER (Estrogen receptor), PR (Progesterone receptor), Ki67, P53, Epidermal growth factor receptor (EGFR), Thyroid transcription factor 1 (TTF-1), P63, Anaplastic lymphoma kinase (ALK), Napsin A, BRAF, Proto-oncogene tyrosine-protein kinase ROS (ROS1), Hepatocyte growth factor receptor (MET), RET, Phosphatidylinositol-3,4,5-trisphosphate 3-phosphatase (PTEN), PD-L1, Prostate specific antigen (PSA), Prostate specific membrane antigen (PSMA), Alpha-methylacyl-CoA racemase (AMACR), Prostatic acid phosphatase (PAP), Prostein (P5015), NKX3.1, CDX2, Carcinoembryonic antigen (CEA), mucins such as mucin 2 (MUC2) and mucin 5AC (MUCSAC), MutL homolog 1 (MLH1), MSH2, MSH6, PSM2 and human epidermal growth factor receptor 2 (HER2).

According to a further embodiment, cancer cell membrane-associated molecules include, but are not limited to human epidermal growth factor receptor 2 (HER2), carcinoembryonic antigen (CEA), prostate-specific antigen (PSA), prostate specific membrane antigen (PSMA), and mucins such as mucin 2 (MUC2) and mucin 5AC (MUCSAC)

In a further embodiment, target markers are markers for gynecological cancers such as breast cancer.

In a further embodiment, target markers are markers for gynecological cancers for breast cancer such as PanC, ER, PR, Ki67, P5, Epidermal growth factor receptor and HER2.

In another further embodiment, target markers are markers for lung cancer such as non-small cell lung cancer.

In a further embodiment, target markers are markers for lung cancer such as TTF-1, P63, ALK, Napsin A, EGFR, BRAF, ROS1, MET, RET, PTEN and PD-L1.

According to a particular embodiment, target markers are markers for gastrointestinal cancers such as colorectal cancers.

In a further embodiment, target markers are markers for colorectal cancers such as thymidylate synthase (TS), CDX2, CEA, MUC2, MUC5AC, MLH1, MSH2, MSH6 and PSM2.

According to a particular embodiment, target markers are markers for urinary track cancers such as bladder cancer.

In a further embodiment, target markers are markers for bladder cancer such as Fibroblast FGFR3 and P53.

According to a particular embodiment, target markers are markers for prostate cancer.

In a further embodiment, target markers are markers for prostate cancer such as PSA, PSMA, AMACR, P63, PAP, P5015 and NKX3.1.

Referring to FIG. 1, is illustrated a method for quantitative measurement of a target marker by in situ immuno fluorescence according to the invention comprising the steps of:

(i) providing a sample (1) immobilized on a sample support (S1);

(ii) carrying out a staining step (S2) comprising incubating said sample with at least one target probe, at least one screening probe for imaging the sample region of interest (first screening probe) and optionally at least one screening probe for the sample region of non-interest to be discarded for further analysis (second screening probe), wherein incubation times of each of said probes with the sample are not higher 3-5 min (typically of about 1-3 min) to obtain a stained sample (2);

(iii) acquiring images of the stained sample comprising imaging a signal emitted by each of the said imaging probes (S3), i.e. the first screening probe signal (C), the second screening probe signal (D) and the target probe signal (T);

(iv) carrying out an image processing step (S4) defining image tiles (4) (e.g. typically regions of about 400×300 µm) based on the obtained images ("tiling") where the tiled image (3) is formed of 1 to n tiles and creating raw files with raw signal values for each imaging probe signal in each pixel (5) of each tile (4) of the tiled image (3);

(v) generating a target evaluation mask comprising an active area for analysis of the target marker, comprising:

a. carrying out a tile-specific threshold determination step (S5) for each screening probe signal in each tile (e.g. CK probe signal and DAPI probe signal);

b. applying the tile-specific thresholding filter (S6) to each pixel (5) within the same tile (4) comprising setting to a first value (e.g. 0) pixels having a screening probe signal beyond the thresholds that need to be discarded and to a second value (e.g. 1) to the retained pixels;

c. obtaining the target evaluation mark (S7) by multiplying the binary value for each pixel of the tile (e.g. 0 or 1) corresponding to the first screening probe signal with the binary value (e.g. 0 or 1) for the same pixel of the tile corresponding to the second screening probe signal to obtain a target evaluation mask (8) (e.g. target epithelial cell mask) for the tile (4), wherein the active area of the mask is defined by pixels comprising signals set to said second value;

(vi) applying the active area of the target evaluation mask on raw values of screening probe signal data and on raw values of the target probe signal data by
   a. multiplying the obtained target evaluation mask (8) of the tile with the raw values of the first screening probe signal and with the raw values of the target probe signal, respectively for the same tile to generate screening probe signal data (9) $C_{11}$ to Cjj (S8$a$) and target probe signal data (10) $T_{11}$ to Tjj (S8$b$), respectively, for each pixel (1 to j) within a tile, where only a raw probe signal in the regions of interest remains (e.g. epithelial cell region);
   b. averaging the pixel data sets of screening probe signals over a tile to an average value $C_{av}$ (e.g. average CK signal) and iterating this process over the N tiles to create a screening probe signal data matrix with all the average values $C_{av}$ ($C_{av11}$ to $C_{avnn}$) for all the tiles (1 to N) to obtain a screening probe data set comprising values proportional to the raw signal values for the first screening probe for the active area;
   c. applying a threshold filter ("autothreshold") to the value of the screening probe signal data matrix comprising setting to a first value (e.g. 0) tiles having a screening probe signal beyond the thresholds and need to be discarded and to a second value (e.g. 1) the retained tiles (S10$a$) to form a filtered first screening probe signal data matrix (13') (e.g. filtered CK data matrix) to obtain a filtered first screening probe data set comprising values proportional to the raw signal values for the first screening probe for the filtered active area;

(vii) Processing the signal of the target probe including
   a. averaging the pixel data sets of target probe signals over the same tile to an average value $T_{av}$ (e.g. average HER2 signal) and iterating this process over the N tiles to create a target probe signal data matrix with all the average values $T_{av}$ ($T_{av11}$ to $T_{avnn}$) for all the tiles (1 to N);
   b. Matching the resulting filtered first screening probe data set on the values of the target probe signal data matrix obtained under step S9$b$ (S10$b$) to form a filtered target probe signal data matrix (14') (e.g. filtered HER2 data matrix) to retain only target probe signal data for the tiles retained on the basis of their first screening probe signal (e.g. signal from the epithelial cell regions) over the entire image (3) to obtain a target probe data set comprising target probe signal values for the active area (viii) carrying out a data binning step on both the filtered first screening probe signal data matrix (13') and the target signal data matrix (14') by setting to a single value all values $C_{avij}$ or $T_{avij}$ within the same range of values to generate values for the first screening probe signal and values for the target probe signal over the tiles retained for analysis to generate a sample output data;

(ix) generating a sample output (S12), wherein said sample output comprises representing the values of the target probe signal versus the values of the first screening probe signal (such as generating a scatter plot (9), step S12$a$), wherein said sample output optionally further comprises the calculation of the ratios of target probe signals over the values of the first screening probe signals for each tile (S12$b$) and optionally a further step of generating a histogram (10) representing the frequencies of occurrence of a particular ratio (value of target probe signal over the value of the first screening probe signal) over the sample (i.e. number of tiles presenting such ratio) normalized to the number of tiles for a given sample (S12$c$);

(x) Optionally generating a score for the sample (S12$d$) by comparing the output of said sample with outputs for a positive control sample (such as a cancer positive case) and a negative sample (non-cancerous sample) obtained by a method of the invention and/or generating a score for the sample by comparing the output of said sample with target marker levels obtained by other methods of marker quantification on reference samples.

Referring to FIG. 1$i$, is provided an illustration of a specific embodiment regarding image processing steps (iv) to (xii) of a method according to the invention:

a) carrying out an imaging processing step (S4) comprising generating surface area units, "tiles" (44) ("tiling") of the images of the sample and creating raw files with raw signal values for pixel of a tile for each imaging probe, wherein for each pixel in a tile, there is a file for raw signals for the CK probe (411), for the signal for the DAPI probe (412) and for the signal of the HER2 probe (413);

b) generating a target evaluation mask comprising
   (i) carrying out a tile-specific threshold determination step (S5) for each screening probe signal, i.e. over the raw signals for the CK probe (411) and for the DAPI probe (412) over a tile;
   (ii) applying the tile-specific thresholding filter (CK and DAPI masks) to each pixel of the same tile (S6) comprising setting to a first value (e.g. zero) the pixels having screening probe signals beyond the thresholds and setting pixels to a second value (e.g. 1), otherwise (retained pixels for further analysis), wherein the retained pixels for the CK probe signal correspond to pixels having a CK probe signal not higher nor lower than the CK tile-specific threshold and the retained pixels for the DAPI probe signal, those not having a DAPI probe signal higher than the DAPI tile-specific threshold;
   (iii) obtaining a target evaluation mask (S7) comprising multiplying for each pixel the binary value of the CK mask (e.g. 0 or 1) with the binary value of the DAPI mask (e.g. 0 or 1) to obtain a tile specific target evaluation mask (epithelial cell mask (81));

c) Applying the active area of the target evaluation mask for a tile by
   (i) multiplying the said tile-specific epithelial cell mask (81) with the pixel raw values of the first screening probe signal (raw CK probe signal value (411)) and with the pixel raw values of the target probe signal (raw HER2 probe signal value (413)), respectively of the same tile to generate a screening probe signal data for each retained pixel and a target probe signal data for each retained pixel;
   (ii) Averaging the raw CK probe signal values of the retained pixels over one tile and the raw CK target probe signal values of the retained pixels over the same tile to obtain a tile-specific average CK signal (111) and an average HER2 signal (121)), respectively (S9$a$ and S9$b$);

d) repeating steps (b) to (c) for each tile of the image of the sample and obtaining data matrices containing the CK data ((13) and HER2 data (14)) for the N tiles;

e) Filtering the values of the data matrices (CK data matrix (13) for the screening probe signal data (S10$a$) to generate a filtered CK data matrix (13'));

f) Processing signals of the target probe comprising matching the filtered CK data matrix on the HER data matrix (14) to retain only the HER2 probe signal values corresponding to the tiles retained in the filtered CK data matrix to generate a filtered HER2 data matrix (14'));

g) Carrying a data binning step (S11) of the values of the data of the obtained filtered matrices ((13') and (14')) to obtain a sample output data matrix;

h) Generating a sample output (S12), based on the obtained sample data output matrix wherein said sample output comprises representing the values of the target probe signal (HER2 probe signal) versus the values of the first screening probe signal (CK probe signal) as a scatter plot (9).

The invention having been described, the following examples are presented by way of illustration, and not limitation.

EXAMPLES

The following abbreviations refer respectively to the definitions below:

FFPE (Formalin-Fixed, Paraffin-Embedded), HE (Hematoxylin and eosin); PBS (Phosphate Buffered Saline).

In order to assess the performance of the method of the invention and its ability to quantitatively score the level of overexpression of a biomarker of interest (in the present case, HER2 protein in breast carcinoma samples is the target marker) data obtained with the method of the invention were compared with the $N_{FISH}$ value and the HER2/CEP17 ratio provided by routine diagnostics as described below.

Example 1: Continuous Signal Quantification of Double IF Staining Using Microfluidic Precision Immunofluorescence Since HER2 protein is situated on epithelial cell membranes and cytokeratin (CK) constitutes a marker for epithelial cells and it has been widely used in carcinomas to distinguish epithelia from stroma (Barak et al., 2004, *Clin. Biochem.*, 37, 529-540; Gustayson et al., 2009, *Arch. Pathol., Lab. Med.*, 133, 1413-1419), the method of the invention is used wherein the staining step (i) is carried out by using a probe for HER2 (target probe) in combination with a probe for CK (first screening probe) to label the sample areas where the expression of HER2 should be interrogated during the fluorescence signal analysis, since it is expressed in epithelial cells.

Then, since the target marker (HER2) is not expressed in the nucleus, a nucleus marker, DAPI, is used as a second screening probe during the staining step in order to label the sample areas where the expression of HER2 should not be interrogated during the fluorescence signal analysis.

A microfluidic tissue processor as described in Ciftlik et al., 2013, *Proc. Natl. Acad. Sci.* 110, 5363-5368 has been used to perform the staining step by immunofluorescence on formalin-fixed paraffin-embedded (FFPE) sections of surgically resected human invasive breast carcinoma samples (FIG. 2A), retrieved from the archives of the Institute of Pathology at the University Hospital of Lausanne (Switzerland) as described below. By clamping the microfluidic microprocessor half-chamber with the tissue slide (FIG. 2B), a shallow flow chamber with a height of 100 μm is formed, allowing fast and uniform delivery and washing of the reagents over a large surface (16×16 mm²) of the tissue section. A distributed microfluidic channel network (250-μm wide microfluidic channels) permitted homogeneous flow throughout the entire chamber and assured that convection was the dominant mechanism for the in-plane bioreagent transport and the method of the invention was performed as described below.

After clamping the microfluidic microprocessor with the glass slide, the staining protocol lasted about 10 minutes in total, including the washing steps, wherein the combined sequential use of Anti-human cytokeratin, clone AE1/AE3 and AF 647 goat anti-mouse IgG (H+L) was used as target probe (primary and secondary antibody, respectively for imaging the target), the combined sequential use of Anti-human c-erbB-2 oncoprotein and AF 594 goat anti-rabbit IgG (H+L) was used as a first screening probe (primary and secondary antibody, respectively for imaging the area of interest) as detailed in Table 1 below:

TABLE 1

| Reagent | Flow duration, s | Incubation time, min | Total time, s |
|---|---|---|---|
| PBS buffer | 10 | — | 10 |
| Anti-human cytokeratin, clone AE1/AE3 | 12 | 2 | 132 |
| PBS buffer | 10 | — | 10 |
| Anti-human c-erbB-2 oncoprotein | 12 | 2 | 132 |
| PBS buffer | 10 | — | 10 |
| AF 594 goat anti-rabbit IgG (H + L) | 12 | 2 | 132 |
| PBS buffer | 10 | — | 10 |
| AF 647 goat anti-mouse IgG (H + L) | 12 | 2 | 132 |
| PBS buffer | 10 | — | 10 |
| Total | 98 | 8 | 578 |

PBS solution, used to wash the chamber in between steps, was delivered at 25 μL/s for 10 seconds. Antibody (Ab) solutions were delivered at 10 μL/s for 12 seconds, and incubated for 2 minutes with a slow flow of 20 nL/s. Upon finalization of the staining protocol, the tissue samples were washed off-chip with deionized water for ten seconds and mounted using 170-μm coverslips using a DAPI-containing solution. For the experimental design related to the incubation time, the typical values of IgG Ag-Ab binding constants were considered as $k_{on}$ (~$10^6$ M$^{-1}$) and $k_{off}$(~$10^{-3}$ s$^{-1}$). The bulk Ab concentration $c_{bulk}$ (~$10^{-8}$M) was chosen large enough so that it is not a limiting factor for the Ab surface coverage and the IF signal in a Langmuir isotherm hypothesis. The binding constants allow to calculate the desorption time $t_d$=1/$k_{off}$ ~$10^3$ s, while the time constant of the recognition reaction is $\tau$=1/($k_{on}$ $c_{bulk}$+$k_{off}$)~$10^2$ s. This forms the basis for the choice of the incubation time at the order of a few minutes.

The tissue slide samples were first incubated with primary antibodies for HER2 and CK, in a sequential manner. In a second step, two fluorescently labeled secondary antibodies as described below were sequentially delivered into the chamber of the microfluidic microprocessor, first for HER2 and then for CK detection. Finally, the slides were washed with deionized water and cover-slipped using a solution containing 4',6-diamidino-2-phenylindole (DAPI) for nuclear counterstaining.

After the staining process, the slides were automatically scanned tile-by-tile (e.g. regions of about 446×335 μm) to obtain a mosaic image in three fluorescent channels, corresponding to the signals of DAPI, CK and HER2, respectively (FIG. 2, B-C).

Study Design

Twenty-five samples from patients were carefully selected to span across a wide range of $N_{FISH}$ values, assessed at the Institute of Pathology according to 2013 ASCO recommendations (Wolff et al., 2013, *J. Clin. Oncol.* 31, 3997-4013). For the analysis by the method of the invention, the 25 cases were grouped into 5 batches that were processed sequentially. One positive (IHC 3+ score) and one negative (IHC 0 score) control sample was included in each batch. The study has been conducted on anonymized tissues.

Tissue Preparation and Reagents

Breast carcinoma samples were obtained as 4 µm FFPE sections mounted on Super Frost Plus slides (Menzel-Glaser, Germany). Tissue samples were first heated for 10 min at 65° C., then dewaxed using Histo-clear (National Diagnostics, GA, USA) for 10 min and rapidly rehydrated using ethanol solutions in decreasing concentrations (100%, 95%, 70% and 40% vol/vol) (Sigma-Aldrich, MO, USA). Subsequently, heat-induced Ag retrieval was done using sodium citrate buffer pH 6 (code: S1699 Dako, Denmark) for 10 min at 95° C. in a hot bath. The samples were then cooled down to room temperature for 20 min and immersed in phosphate buffered saline pH 7.4 (PBS) (Sigma Aldrich, MO, USA).

The histological slides were inserted into the device to run the staining assay. PBS was used as a buffer for cleaning and priming of the fluidic path. Double-staining was performed using rabbit anti-human c-erbB-2 oncoprotein (code: A0485, Dako, Denmark) and mouse anti-human cytokeratin, clone AE1/AE3 (code M3515, Dako, Denmark), as primary antibodies, with a concentration of 1.28 µg/mL and 1.02 µg/mL, respectively. For fluorescent detection, Alexa Fluor 594 goat anti-rabbit IgG (H+L) (code: A-11037, Life Technologies, CA, USA) and Alexa Fluor 647 goat anti-mouse IgG (H+L) (code: A-21236, Life Technologies, CA, USA) secondary antibodies, at a concentration of 50 µg/mL, were employed. Nuclear counterstaining was realized using DAPI, included in Fluoroshield (code: F6057, Sigma Aldrich, MO, USA) mounting solution. All the antibodies were dissolved in a 0.05% (vol/vol) solution of Tween 20 (code: P137-9, Sigma Aldrich, MO, USA) in PBS.

Device Setup

The microfluidic microprocessor (MTP) formed a fluidic halve-chamber that was reversibly clamped with a tissue slide using the force provided by a permanent magnet. When forming the MTP-glass slide fluidic chamber, the histological glass slide was clamped against the MTP via a polydimethylsiloxane gasket, both to fix the height of the reaction chamber to 100 µm and to prevent leakage. For interfacing the MTP with external fluidic control systems, a polymethylmetacrylate holder was assembled with the MTP. Fluid manipulation was realized using five syringe pumps (Cetoni, Germany) that were filled with the required reagents and connected to the inlet of the MTP via the holder.

Routine Diagnostic Analysis

For routine determination of HER2 status of breast cancer cases, IHC was performed on 4 µm FFPE sections on the Ventana Benchmark automat (Ventana Medical Systems, AZ, USA). The samples were stained using Ventana anti-HER2/neu Ab (clone: 4B5) and scored according to current ASCO/CAP guidelines (Wolff et al., 2013, supra). FISH was done manually on 4 µm FFPE sections using the PathVysion HER-2 DNA probe kit (Abbott Molecular, IL, USA). Signal analysis was performed on a minimum of 40 nuclei per case after screening of the whole section.

Fluorescence Image Acquisition

Slides were inserted in an automated epi-fluorescent microscope (Axio Imager M2m, Zeiss, Germany) and mosaic images were obtained using a CCD (charge-coupled device) camera. Images in three fluorescent channels, corresponding to the signals of DAPI, CK and HER2, respectively, were automatically obtained. Autofocusing, acquisition, scanning and stitching were done automatically. Prior to analysis, all images were checked if they contained artifacts that could influence the analysis. Based on this assessment, cases 22 and 25 were removed from the dataset due to the lack of epithelial cells in the stained slide that eventually resulted in a Gaussian fit with a low adjusted $R^2$ value of 0.4837 and 0.4806, respectively. The average image acquisition varies from 10 to 40 minutes, depending on the size of the sample.

Example 2: Analysis of the Scanned Tiles

Each tile from the resulting mosaic images obtained as described above was then analyzed by running an image-processing method as described in FIG. 1 which identified locations of CK expression and created a region of interest to limit the interrogation of the HER2 signal to epithelial areas only ("CK mask"). Information from the DAPI channel was used to remove the nuclei from the interrogation zones ("DAPI mask"), as the HER2 and CK markers of interest are not expressed in the nuclei.

The steps used in the analysis of the obtained images can be schematized in FIG. 1.

OriginLab software (OriginLab Corporation, MA, USA) was used to obtain scatter plots, histograms and statistical values. The image-processing step comprising the whole process from creating binary masks for each image sub-element to the formation of scatter plots (steps S5 to S12) takes approximately 20 minutes per batch, giving an average of 3 minutes per sample.

As a result of the tile processing, 2D scatter plots were obtained, in which the averaged HER2 and CK signals per tile were represented as points. FIG. 2D is an example of such scatter plot, in which an IHC HER2 2+ (equivocal) case is compared to a 3+ and a 0 case, the latter two being used as positive and negative controls, respectively. The data from each scatter plot were subsequently processed to provide statistical indicators of HER2 expression as described in FIG. 1g, which finally resulted in a sample scoring through the method of the invention ('MTP-score').

In order to compare the information contained in the scatter plot signatures of HER2 protein expression for breast cancer cases obtained by a method of the invention, the corresponding HER2 copy number was obtained by routine FISH as follows: Routine FISH analysis on the same samples gave a wide range of HER2 gene copy numbers ($N_{FISH}$) ranging from 1.9 to 15 (Table 2) where comparison is made between:

i) IHC scoring following 2013 ASCO/CAP guidelines (Wolff et al., 2013, supra);

ii) $N_{FISH}$;

iii) HER2/CEP17 ratio;

iv) HER2 status classification based on $N_{FISH}$; and v) HER2 status classification according to 2013 ASCO/CAP guidelines (Wolff et al., 2013, supra).

Table 2 shows the classification of IHC results for these 25 cases following the 2013 ASCO/CAP interpretation guidelines (Wolff et al., 2013, supra) by two blinded experienced pathologists. By routine HER2 FISH analysis, based on the $N_{FISH}$ values, 10 cases out of the 25 were classified as negative ($N_{FISH}$<4), 9 cases as positive ($N_{FISH}$ ≥6), and 6 cases as equivocal (4≤$N_{FISH}$<6) (Neg., Pos., and Equ., respectively, in FIG. 5). Although the 2013 ASCO/CAP guidelines for HER2 status classification also take into account the HER2/CEP17 ratio, it was decided for the purpose of this study to focus on the correlation between HER2 protein expression and $N_{FISH}$.

Case 13 was removed from the dataset in FIG. 7 since a control HE slide showed that only ductal carcinoma in situ (DCIS) was left on the sections used for the study. Similarly, case 14 was removed from the dataset in FIG. 7 because the section presented heterogeneous HER2 status, resulting in two $N_{FISH}$ values. For cases 22 and 25, interpretation of routine IHC on the resected tumor specimen failed due to repeated tissue detachment from the glass slide. The IHC score indicated for these cases is the one found on the initial core biopsy.

TABLE 2

| Case | i) IHC scoring | ii) $N_{FISH}$ | iii) HER2/CEP17 ratio | iv) HER2 status based on $N_{FISH}$ | v) HER2 status classification |
|---|---|---|---|---|---|
| 1 | 2+ | 1.9 | 0.76 | negative | negative |
| 2 | 2+ | 2.25 | 1.06 | negative | negative |
| 3 | 1+ | 2.30 | 1.01 | negative | negative |
| 4 | 1+ | 2.38 | 1.29 | negative | negative |
| 5 | 1+ | 2.54 | 1.20 | negative | negative |
| 6 | 0 | 2.70 | 1.19 | negative | negative |
| 7 | 0 | 2.80 | 1.22 | negative | negative |
| 8 | 2+ | 2.90 | 1.12 | negative | negative |
| 9 | 2+ | 3.10 | 1.60 | negative | negative |
| 10 | 1+ | 3.30 | 1.38 | negative | negative |
| 11 | 2+ | 4.38 | 1.80 | equivocal | equivocal |
| 12 | 3+ | 4.64 | 1.48 | equivocal | positive |
| 13 | 2+ (only DCIS left) | 4.85 | 2.09 | equivocal | positive |
| 14 | 2+ | 4.90/2.50 | 2.7/1.3 | equivocal (heterogeneous) | positive (heterogeneous) |
| 15 | 1+ | 4.90 | 2.30 | equivocal | positive |
| 16 | 1+ | 5.80 | 2.80 | equivocal | positive |
| 17 | 2+ | 6.13 | 2.08 | positive | positive |
| 18 | 2+ | 6.80 | 1.80 | positive | positive |
| 19 | 3+ | 7.60 | 3.30 | positive | positive |
| 20 | 3+ | 9.35 | 5.30 | positive | positive |
| 21 | 3+ | 9.40 | 2.60 | positive | positive |
| 22 | 3+ | 10.70 | 4.90 | positive | positive |
| 23 | 3+ | 13.00 | 3.40 | positive | positive |
| 24 | 3+ | 15.00 | 3.00 | positive | positive |
| 25 | 3+ (on the core biopsy) | 15.00 | 7.50 | positive | positive |

Scatter Plot Signatures 25 invasive breast carcinoma cases were selected and grouped into 5 batches and they were all processed in a batch sequentially in one experimental run according to the method of the invention, while one positive (IHC 3$^+$ score) and one negative (IHC 0 score) control sample were each time included in the batch.

Figure 1A:
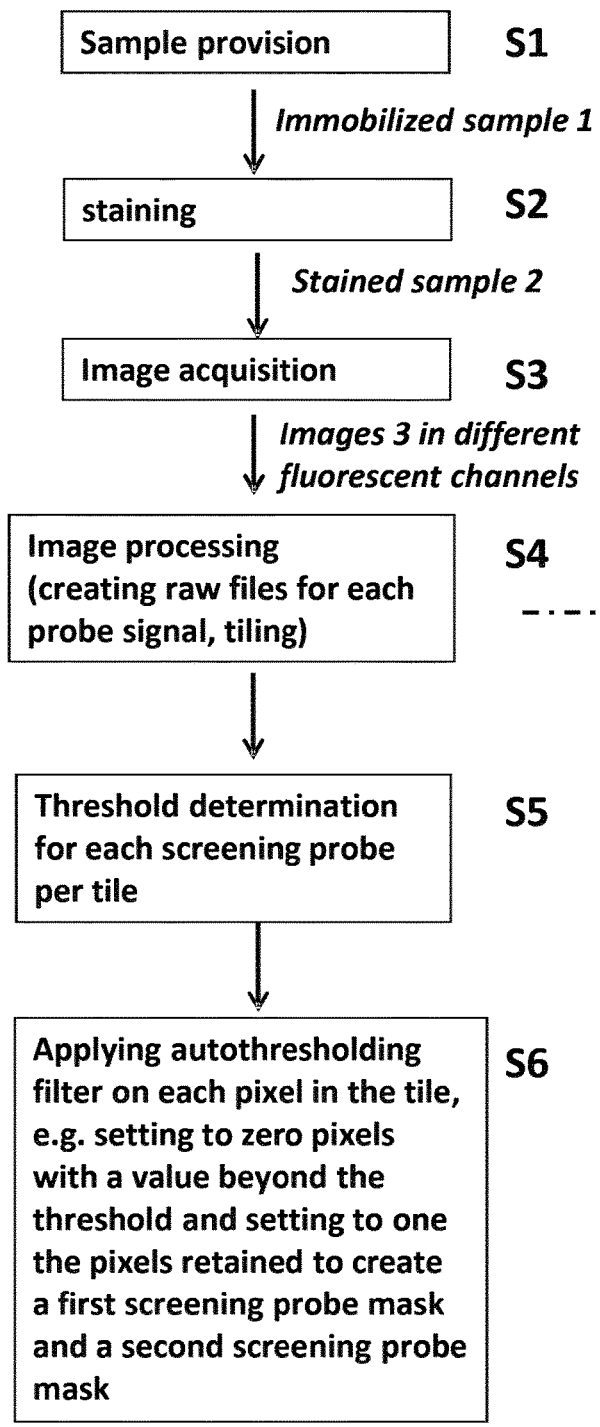
FIG. 1 is an illustration of the steps used in an embodiment of a method of the invention as described in Examples 1 and 2. Images, tiles and pixels are illustrated schematically, the tiles and pixels representing image signal information, in particular fluorescence signal information. Tiles and pixels are illustrated in a contiguous arrangement; however, tiles and pixels may represent signal information in a contiguous image area, or in a non-contiguous image area. Also, the tiles and pixels may represent a same geometric area over the sample surface or a plurality of non-contiguous geometric areas over the sample surface.
Figure 1A:
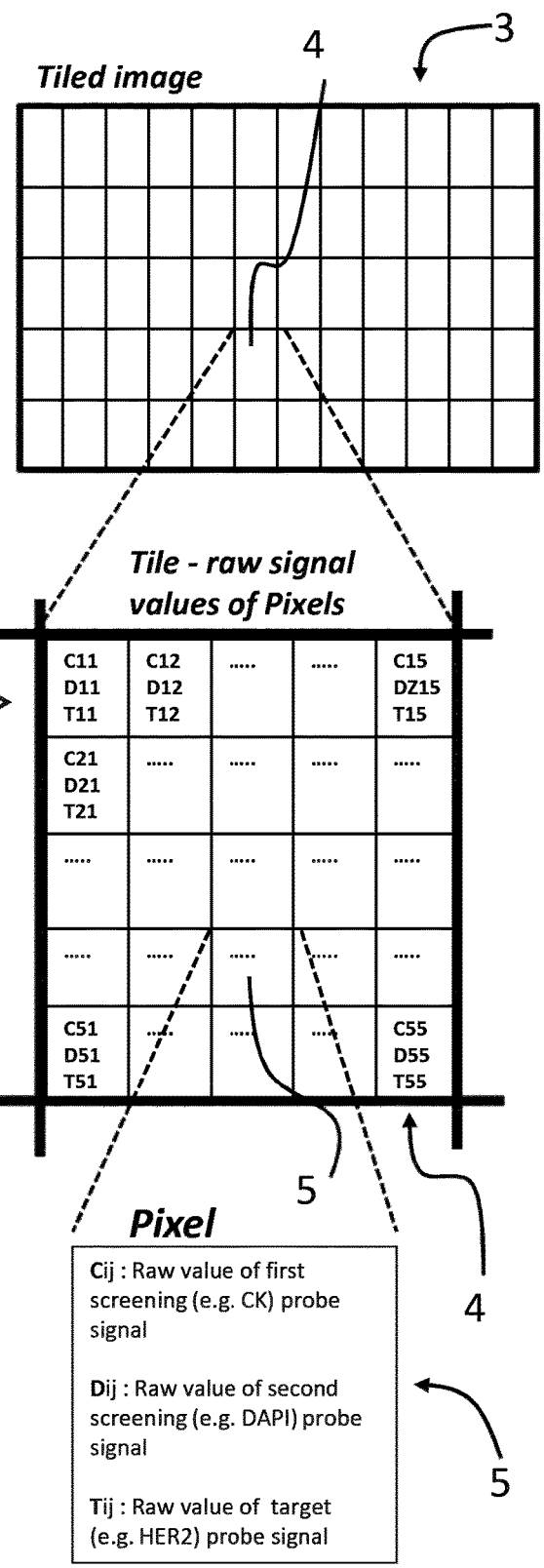
Figure 1E:
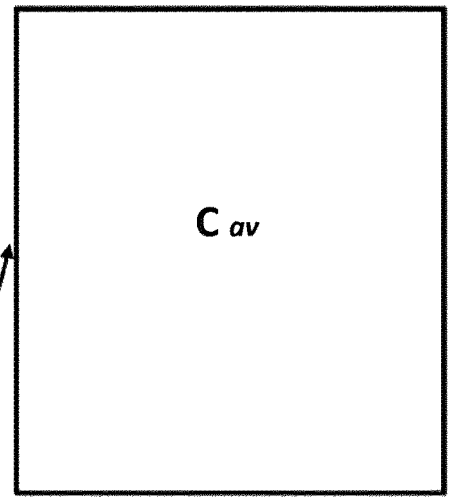
Figure 1E:
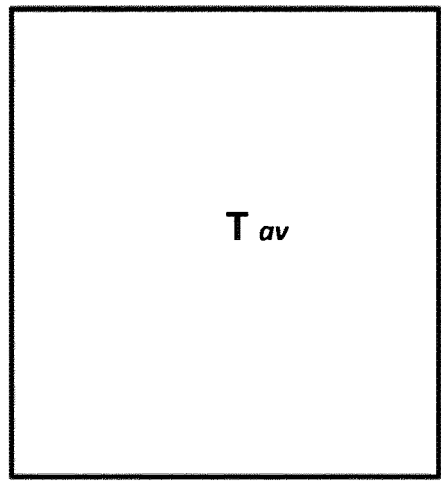
Figure 1F:
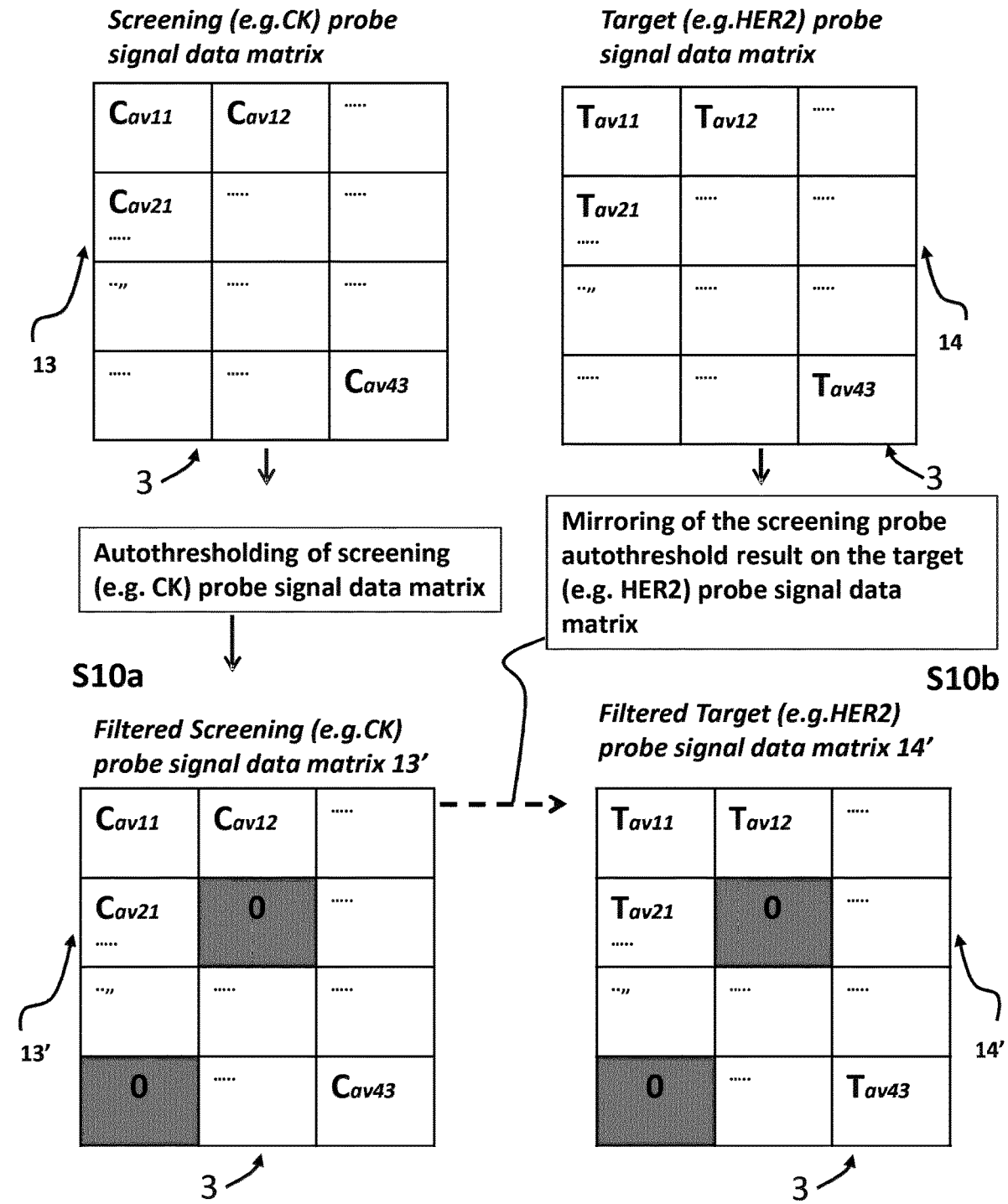
Figure 1G:
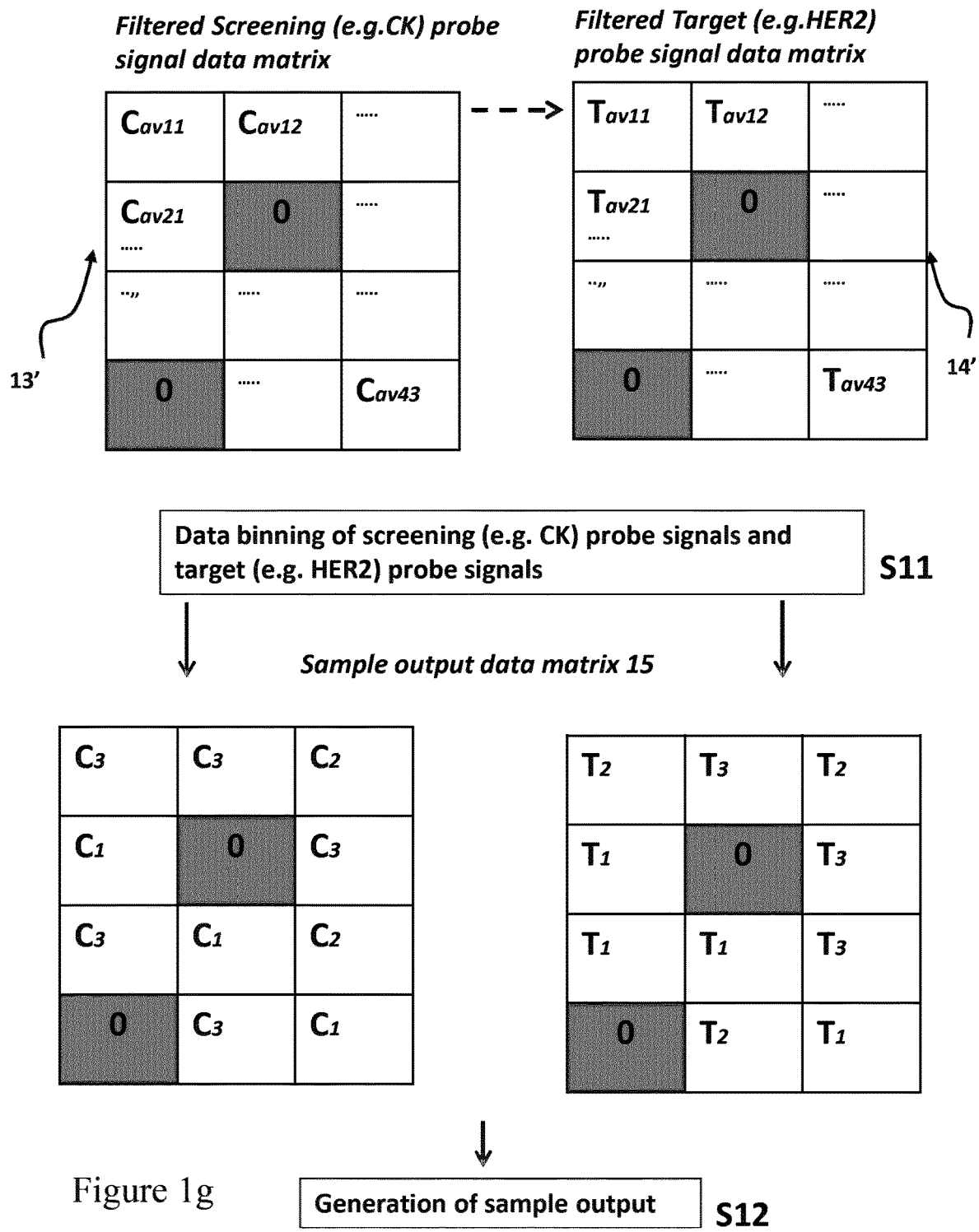
Figure 1I:
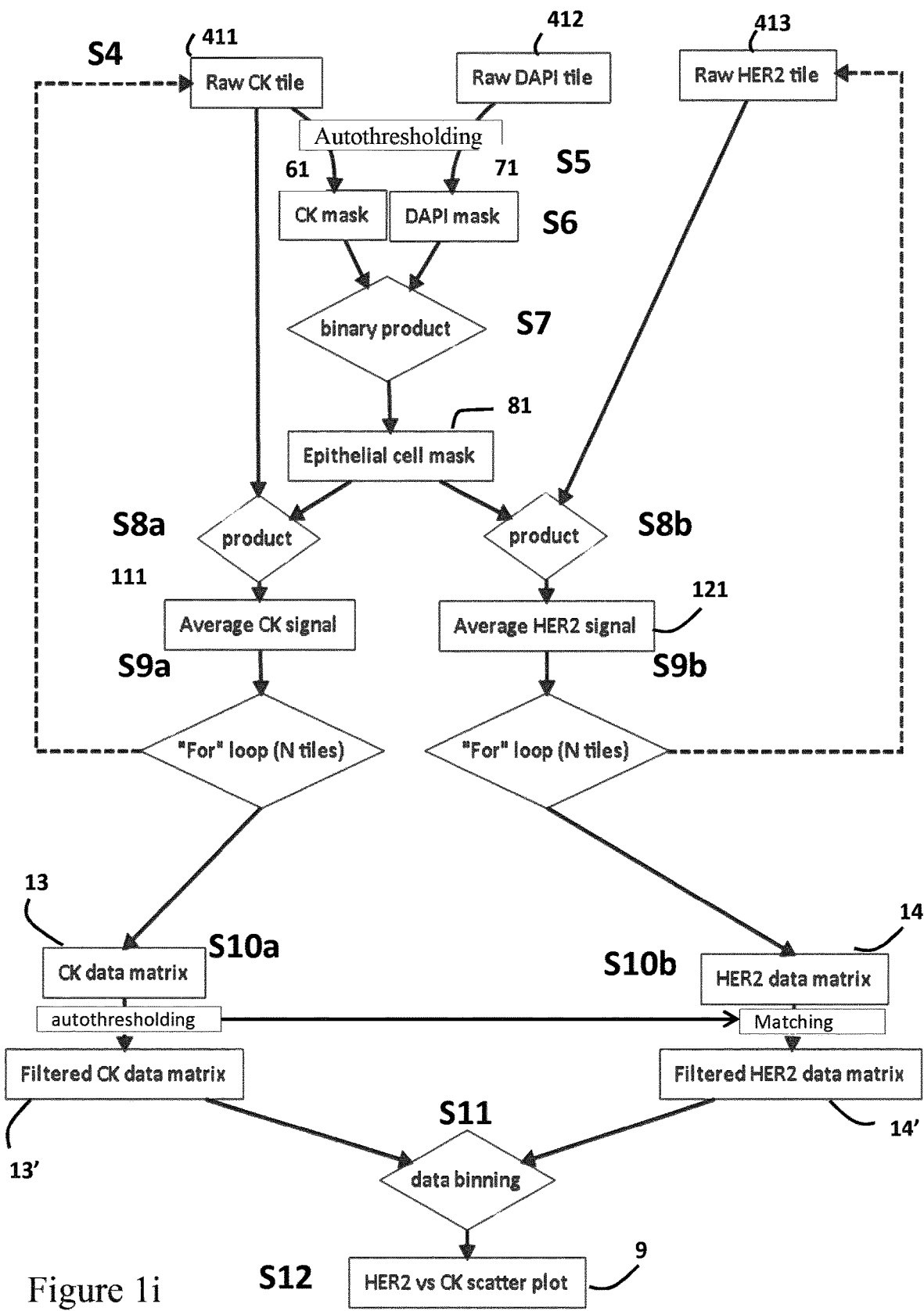

The steps of the method according to the invention for the analysis of the obtained image was automated in the form of an algorithm in order to determine the regions of interest with epithelial cells and remove the background, as illustrated in FIG. 1i, for each tile of the mosaic image of a given sample. This resulted in one average HER2 and CK signal per tile, which is represented by a point in a scatter plot for each patient. The scatter plot shows the correlation between the tile-averaged HER2 and CK signals (a), compared with the scatter plot data obtained from the IHC 3+(b) and IHC 0 (c) control samples of the batch. The MTP score for each patient obtained as described below clearly correlated with $N_{FISH}$ obtained from routine analysis.

Scatter Plot Comparison

To exploit the scatter plot data, of which three examples are shown in FIG. 5, the scatter plot of a case under interrogation was compared to scatter plots obtained from absolute negative and positive control cases by following the following steps:

i) Calculating the ratio between HER2 and CK signals on a tile-by-tile basis;

ii) Representing the thus obtained data array as a histogram, representing the frequency of occurrence of a given HER2/CK ratio normalized to the number of tiles.

FIG. 6 shows as examples the histograms obtained for five patients, to whom prior routine analysis attributed the following IHC scores: 3+ (a), 0 (b), and three cases (c1-c3) from which two scored as 2+ and one as 3+ and had $N_{FISH}$ values of 1.9, 4.4, and 9.4, respectively. The positive and negative controls were used as references of the expected HER2 signal intensities for each sample. For the three samples represented in c1-c3, the histograms shifted more towards the right as the $N_{FISH}$ increased, indicating an average increment in the acquired HER2 signal with respect to CK, when the number of HER2 gene copies was higher. Moreover, the widening of the histogram for high $N_{FISH}$ cases showed that the overexpression of HER2 also corresponded to a larger dispersion of the HER2 signal. A Gaussian fit of a histogram allowed determining the mean HER2/CK value and normalizing this by the mean obtained for the IHC 3+ control sample in the batch defined the M-score. Similarly, the standard deviation ($\sigma$) was extracted from the Gaussian fit of a histogram and normalized it by the $\sigma$ value of the positive control of the batch to define the $\Sigma$-score.

Finally, the defined score (MTP-score) was determined for each sample as the product of the M- and $\Sigma$-scores. The three scores found by this analysis showed Pearson correlation coefficients of at least 0.9 against the $N_{FISH}$ values obtained by routine FISH analysis. FIG. 7 shows the score values obtained using the method of analysis over the full set of cases used in this study. The M-, E-, and MTP-scores obtained a Pearson coefficient $\rho$ of 0.90, 0.90, and 0.93, respectively, and an increasing exponent $\alpha$ of the power law fit ($y \sim x^\alpha$).

The score for each patient clearly correlated with $N_{FISH}$ obtained from routine analysis. At first sight already, the scatter plots of FIG. 5 show that the samples assigned a low NFISH value (<~3) have a linear correlation of HER2 with CK, while for NFISH>~5, HER2 values get systematically higher and more dispersed.

This correlation demonstrates that MTP-scoring based on the method of the invention can indeed deliver quantitative information on the overexpression of HER2, which as precise as the gene copy number obtained by FISH.

Altogether, the presented data support that a method of the invention proved to be very powerful in terms of quantifying target marker expression in histopathological tissue sections, significantly increasing the precision of the information that can be obtained by an immunoassay. In particular, experiments showed that HER2 biomarker quantification, as obtained by the presented method, can provide molecular information that is as precise as data obtained by FISH tests, while keeping the cost and time advantage of an IF assay.

The linearity of the staining, combined with low-complexity image analysis, allowed to establish a continuous scoring that linearly followed the gene copy number as assessed by in situ hybridization.

Interestingly, for cases 6, 9 and 14 in this study, heterogeneity was detected by both technical approaches. Routine IHC followed by FISH analysis demonstrated two areas of the tissue expressing/amplifying HER2 at different levels. On the other hand, the scatter plots obtained using the method of the invention showed that there are 2 distinct populations with different levels of HER2 expression, in comparison to a negative $N_{FISH}$.

It also shows that gene copy number gain is not always sufficient for protein overexpression. The scatter plot of case 15 with $N_{FISH}$ value of 4.9 correlates more with the HER2-negative control signature with MTP-scores less than 0.1, suggesting that although there is a moderate copy number gain, there is no significant protein overexpression. Indeed, case 15 was considered equivocal/positive by FISH analysis, even though the IHC score was +1 (Table 2).

Therefore, a method of the invention and the integration of the obtained information to routine diagnostic workflows may imply a major leap towards the concretization of precision medicine and the so-obtained quantitative data can be used as a scoring aid to pathologists, to increase success of treatment response prediction and prognosis and can be applied to other markers in the field of cancer diagnostics.

Determination of the Regions of Interest for Interrogation of the HER2 Signal

The CK channel could be used to define the areas where the expression of HER2 should be interrogated. ImageJ macros were applied tile-by-tile (n=40482) for the purpose of automation of the image processing algorithm.

However, if in HER2-overexpressing samples (FIG. 3B), the use of the HER2 signal alone would be clearly sufficient to determine the regions of interest, for tumors that do not strongly overexpress HER2 (FIG. 3C), it would be difficult to distinguish epithelial cells from surrounding parts in the tissue. Especially in these cases, employing the signal in the CK channel allowed to ensure that the regions of interest for the interrogation of the HER2 signal corresponded to epithelial cells, independently from the intensity of the HER2 signal.

As a result, every tile was first assigned an average signal value for the CK and HER2 signals. The thus obtained CK signal intensities were then analyzed and filtered, in a case-by-case fashion, in order to remove the tiles that had none or a few epithelial cells from further analysis. In particular, tiles which showed a CK average below a given threshold were automatically filtered out from the dataset (autothresholding) as shown on FIG. 4.

Finally, de facto establishing an upper threshold of the CK signal, 5% of the brightest tiles was removed for each case, to account for possible artifacts like small agglomerates of fluorophores that eventually result in the saturation of the fluorescent signal intensity.

Consequently, all tiles that showed a CK value above the lower and below the upper thresholds were kept for further analysis.

Example 3: Comparison with Long Incubation Time Method

In order to assess the precision of the obtained IF staining with respect to conventional methods with longer incubation times, fluorescently labeled antigens (Ag) were immobilized on the surface of a glass slide with various volume concentrations, which ranged from 0 to 1'000 µg/mL.

As depicted in FIG. 8, long incubation times of one hour for manual assays resulted in a non-linear relationship between the Ag fluorescent signal and its Ab, showing sudden Ab signal saturation with respect to its Ag concentration. On the contrary, when the incubation time for the Ab-Ag reaction was limited to 2 minutes, a signal from the antibodies that was more proportional to that of the Ags was obtained. The linear fit of the Ab-Ag signal plotted in FIG. 8F resulted in a regression coefficient of 0.96. This experiment was performed using fluorescently labeled IgG and showed the advantage of reducing the incubation times (e.g. by using precise microfluidic IF) when compared to current standard protocols that use incubation times ranging from 30 minutes to a few hours. Even though the characteristics of the IgG spotting experiments do not fully correspond to those of the tissue, the recognition process is also based on an Ag-Ab interaction at a surface, like on a tissue slide. The implementation of a spotting microarray allowed obtaining a direct fluorescence signal from the Ags and compare it to the signal from the recognizing Abs in an analytical fashion.

On top of this, this assay allowed to create a controlled gradient of Ag concentrations on the same slide, which is not possible with tissue sections. Finally, a second incubation was performed with antibodies that recognized the previously incubated IgGs. The results also manifested that a short incubation time of 2 minutes gives a signal that is more proportional to the Ag concentration than an incubation time of one hour and that the IF signal was more proportional to the antigen concentration than what could be obtained by traditional IHC methods.

The influence of the incubation time was further validated by performing an off-chip protocol with long incubation times (typically 1 hour) for the staining of actual tissue samples, after which IF was assessed using the same automatic image analysis protocol.

FIG. 9 shows the histograms of the HER2/CK ratio for several cases, either obtained with (i) the using short incubation times (at the order of a few minutes), or (ii) the off-chip protocol using an incubation time of 1 hour. It can be seen that the histograms become broader and shift to higher HER2/CK ratios for cases treated with the long incubation time, rendering a less accurate assessment of the HER2 expression level, as evidenced in the plot of the M-score (FIG. 9B) and the Σ-score (FIG. 9C), especially for $N_{FISH}$<6, which is the interval for which equivocal results are encountered.

These results show that the obtained automated scores when using long incubation times have little or no diagnostic value for low $N_{FISH}$ values, the interval where quantitative results are most required in practical diagnostics. Using short incubation times with a method of the invention not only solves this problem but also provides a much more proportional score to quantitative results obtained with in-situ hybridization in the whole diagnostic range.

The invention claimed is:

1. A method for quantitative measurement of a target marker by in situ immuno fluorescence comprising the steps of:
    a) providing a sample immobilized on a sample support;
    b) carrying out a staining step comprising incubating said sample with at least one target probe, at least one screening probe for imaging the sample region of interest (first screening probe) and optionally at least one further screening probe for the sample region of non-interest to be discarded in further analysis (second screening probe), wherein incubation times of the sample with each of said probes are sufficiently low to avoid saturation of the sample with the probes, while ensuring suitable staining of the sample so that a linear relationship between the target marker concentration and the resultant fluorescent signal intensity can be formed, wherein incubation times of the sample with each of said probes are less than 16 minutes;

c) acquiring an image of the stained sample comprising raw signals emitted by each of the imaging probes;

d) generating a target evaluation mask comprising an active area for analysis of said target marker, comprising defining a threshold for signals of said at least one screening probe, and assigning binary values to screening probe signals, said binary values comprising a first value and a second value, whereby screening probe signal values that are beyond said corresponding threshold are set to said first value, and screening probe signal values that are not beyond said corresponding threshold are set to said second value, said active area of the mask being defined by areas of the image comprising signals set to said second value;

e) applying the active area of the target evaluation mask on the raw signal values of the first screening probe to obtain a screening probe data set comprising values proportional to the raw signal values of the first screening probe for the active area;

f) processing signals of the target probe, including extracting target probe signal data limited to said active area to obtain a target probe data set comprising target probe signal values for the active area; and g) generating a sample output including combining said target probe data set with said screening probe data set to provide information on quantitative levels of the target marker.

2. The method according to claim 1, wherein said incubation times are less than 8 minutes.

3. The method according to claim 2, wherein said incubation times are less than 5 minutes.

4. The method according to claim 1 further including:
processing said image before generating said target evaluation mask, comprising defining tiles representing surface area portions of the image; and
effecting steps (d) and (e) on each tile.

5. The method according to claim 4, wherein a threshold is defined for each tile.

6. The method according to claim 4, wherein a threshold for a corresponding tile is defined by means of an auto-thresholding algorithm applied over said corresponding tile.

7. The method according to claim 1, wherein said raw signals emitted by each of the imaging probes are raw signals of pixels of the image and wherein assigning screening probe signals to a first value or to a second value is performed on each pixel.

8. The method according to claim 4, comprising in step (e), calculating, for each tile, an average of the values proportional to the raw signal values of the first screening probe for the active area, to obtain an average first screening probe signal value (111) per tile.

9. The method according to claim 1, further comprising a second screening probe.

10. The method according to claim 9, comprising defining a threshold for signals of said second screening probe, and assigning said binary values to the second screening probe signals, whereby second screening probe signal values that are beyond said corresponding threshold are set to the first value, and second screening probe signal values that are not beyond said corresponding threshold are set to the second value.

11. The method according to claim 10, wherein said generating a target evaluation mark comprises multiplying the binary values corresponding to the first screening probe signals with binary values corresponding to the second screening probe signals.

12. The method according to claim 1, further including in step (e), filtering the screening probe data set, said filtering comprising defining a data set threshold and excluding data of the screening probe data set that are beyond said data set threshold, to obtain a filtered screening probe data set for a filtered active area.

13. The method according to claim 11, including filtering the target probe data set, said filtering comprising excluding data of the target probe data set such that a filtered active area covered by the filtered target probe data set matches the filtered active area covered by the filtered screening probe data set.

14. The method according to claim 1, comprising in step (f), applying the active area of the target evaluation mask on the raw signal values of the target screening probe to obtain values proportional to the raw signal values of the target probe for the active area.

15. The method according to claim 14, including: calculating, for each tile, an average of the values proportional to the raw signal values of the target probe for the active area, to obtain an average target probe signal value (121) per tile.

16. The method according to claim 1, wherein in step (g), generating sample output comprises any one or more of:
representing in a graph, for instance in the form of a scatter plot (9), values of the target probe signal versus values of the first screening probe signal;
generating a histogram (10) representing the frequencies of occurrence of a ratio of target probe signal over the first screening probe signal for the sample;
generating a score for the sample by comparing the output of said sample with outputs for a positive control sample and a negative control sample;
generating a score for the sample by comparing the output of said sample with target marker levels obtained by other methods;
calculating ratios of target probe signals over the values of the first screening probe signals for each tiles, and displaying;
generating a histogram (10) representing the frequencies of occurrence of a ratio of target probe signal over the first screening probe signal for the sample normalized to the number of tiles for a given sample.

17. The method according to claim 1, wherein:
the first screening probe is an imaging probe for a marker of epithelial cells, for instance the first screening probe comprises an antibody specific for cytokeratin;
the target probe is an imaging probe for a membrane-associated molecule of a cancer cell;
optionally, the second screening probe is an imaging probe for a marker for the cells' nucleus.

18. The method according to claim 1, wherein the elution step or washing step are conducted at a flow rate between 0.2 nl/s and 25 µl/s.

19. The method according to claim 1, wherein the incubation between each of said probes and the sample is conducted at a temperature from 25 to 60° C.

* * * * *

UNITED STATES PATENT AND TRADEMARK OFFICE
CERTIFICATE OF CORRECTION

PATENT NO. : 10,509,945 B2
APPLICATION NO. : 16/075998
DATED : December 17, 2019
INVENTOR(S) : Diego Gabriel Dupouy et al.

It is certified that error appears in the above-identified patent and that said Letters Patent is hereby corrected as shown below:

In the Specification

Column 10,
Line 5, "N $F_{FISH}$" should read --$N_{FISH}$--.
Line 7, "N $F_{FISH}$" should read --$N_{FISH}$--.

Column 11,
Line 47, "mucin SAC (MUCSAC)" should read --mucin 5AC (MUC5AC)--.
Lines 55-56, "(MUCSAC)" should read --(MUC5AC)--.

Signed and Sealed this
Ninth Day of June, 2020

Andrei Iancu
*Director of the United States Patent and Trademark Office*